(12) United States Patent
Durant et al.

(10) Patent No.: US 7,041,702 B1
(45) Date of Patent: May 9, 2006

(54) PHARMACEUTICALLY ACTIVE COMPOUNDS AND METHODS OF USE

(75) Inventors: Graham J. Durant, Plymouth (GB); Seetharamaiyer Padmanabhan, Malden, MA (US)

(73) Assignee: Scion Pharmaceuticals, Inc., Medford, MA (US)

( * ) Notice: Subject to any disclaimer, the term of this patent is extended or adjusted under 35 U.S.C. 154(b) by 0 days.

(21) Appl. No.: 09/176,067

(22) Filed: Oct. 20, 1998

Related U.S. Application Data

(60) Provisional application No. 60/064,830, filed on Oct. 21, 1997.

(51) Int. Cl.
```
A61K 31/47    (2006.01)
A61K 31/41    (2006.01)
A61K 31/40    (2006.01)
A61K 31/38    (2006.01)
A61K 31/34    (2006.01)
```

(52) U.S. Cl. ............. 514/617; 514/618; 514/622; 514/623; 514/311; 514/314; 514/355; 514/414; 514/415; 514/448; 514/471; 564/161; 564/162; 564/170; 564/174; 564/176; 564/177; 564/179; 564/182; 564/183; 564/184; 564/185; 546/165; 546/277.4; 546/280.4; 546/283.4; 546/332; 548/454; 548/455; 548/465; 548/491; 549/72; 549/487

(58) Field of Classification Search ......... 564/185; 514/617
See application file for complete search history.

(56) References Cited

U.S. PATENT DOCUMENTS

| | | | | |
|---|---|---|---|---|
| 3,972,872 | A | 8/1976 | Hamanaka | 260/239.1 |
| 4,156,734 | A | 5/1979 | Stone | 424/273 R |
| 4,544,670 | A * | 10/1985 | Studt et al. | 514/617 |
| 5,741,661 | A | 4/1998 | Goldin et al. | 435/29 |
| 5,955,507 | A | 9/1999 | Durant et al. | 514/634 |
| 6,013,675 | A | 1/2000 | Durant et al. | 514/634 |
| 6,025,355 | A | 2/2000 | Reddy et al. | 514/224.2 |

FOREIGN PATENT DOCUMENTS

| | | |
|---|---|---|
| DE | 24 33 625 | 1/1975 |
| DE | 25 31 343 A1 | 2/1977 |
| DE | 25 45 647 A1 | 4/1977 |
| DE | 27 33 440 A1 | 2/1978 |
| DE | 28 02 757 A1 | 7/1979 |
| EP | 0 062 844 A1 | 10/1982 |
| FR | 2.222.375 A1 | 10/1974 |
| WO | WO 94/27591 | 12/1994 |
| WO | WO98/06401 | 2/1998 |

OTHER PUBLICATIONS

Okajima et al. Chem. Abst. 115:29165, 1991.*
Fukada et al., Chem Abst. 105:152653, 1986.*
Augustin et al., Chem. Abst. 100:138782, 1984.*
Gund et al. Chem. Abst. 77:163827, 1972.*
Malyuga et al. Chem. Abst. 74:136938, 1971.*
Neidlein et al., Chem. Abst. 67:100033, 1967.*
Buscemi et al., "Heterocyclic Photorearrangements. Photochemical Behavior of Some 3,4-Disubstituted 1,2,4-Oxadiozoles in Methanol at 254 nm", *Journal of Hetrocyclic Chemistry*, May-Jun. 1988, vol. 25, No. 3, pp. 931-935.
Buschauer, V.A., "Synthese und pharmakologische Wirkung von Arylmethylthioethylguanidinen", *Arzneimittel Forschung*, Sep. 1987, vol. 37, No. 9, pp. 1008-1012.
Gund et al., "A Novel Reaction of Guanidine with Benzaldehydes", *Tetrahedron Letters*, Sep. 1972, No. 38, pp. 3983-3986.
Mitsunobu et al., "Preparation and Reactions of N-Benzoyl- and N- Ethoxycarbonylcarbodiimides", *Bulletin of the Chemical Society of Japan*, Dec. 1972, vol. 45, No. 12, pp. 3607-3611.
Nagasawa et al., "Alkylation of Thioureas and Related Compounds by Use of Alcohols, Diethyl Azodibarboxylate, and Triphenylphosphine", *The Chemical Society of Japan*, Jul. 1981, vol. 54, No. 7, pp. 2223-2224.
Nakayama et al., "Synthesis and Structure-Activity Study of Protease Inhibitors", *Chemical Pharmaceutical Bulletin*, Jan. 1993, vol. 41, No. 1, pp. 117-125.
Okajima et al., "Synthesis and Reaction of 2-Imino-1, 3-thiazetidines and 2-Imino-1, 3-dithietanes", *Journal of Heterocyclic Chemistry*, Jan. 1991, vol. 28, No. 1, pp. 177-185.
Schneller et al., "Synthesis of proximal-Benzoguanine and a Simplified Synthesis of proximal-Benzohypoxanthine", *Journal of Organic Chemistry*, 1986, vol. 51, No. 21, pp. 4067-4070.
Trumm et al., "Tetrahydroisochinoline als Bausteine von H2-Antagonisten", *Arzneimittel Gorschung*, Aug. 1986, vol. 36, No. 8, pp. 1169-1174.
Yamazaki et al., "Synthesis of Guanosine and Its Derivatives from 5-Amino-1-beta-D-ribofuranosyl-l-imidazolecarboxamide", *Journal of Organic Chemistry*, Jun. 1967, vol. 32, No. 6, pp. 1825-1828.

* cited by examiner

*Primary Examiner*—Peter O'Sullivan
(74) *Attorney, Agent, or Firm*—Edwards Angell Palmer & Dodge LLP; Jeffrey D. Hsi; Christine C. O'Day

(57) ABSTRACT

The present invention relates to pharmaceutically acceptable compounds, including acylguanidine compounds, and methods of treatment and pharmaceutical compositions that utilize or comprise one or more such compounds. Compounds of the invention are particularly useful for the treatment or prophylaxis of neurological injury and neurodegenerative disorders.

1 Claim, No Drawings

PHARMACEUTICALLY ACTIVE COMPOUNDS AND METHODS OF USE

CROSS-REFERENCE TO RELATED APPLICATIONS

The present application is a continuation-in-part of U.S. provisional application 60/064,830, filed Oct. 21, 1997, which application is incorporated herein by reference in its entirety.

BACKGROUND OF THE INVENTION

1. Field of the Invention

The present invention relates to pharmaceutically active compounds, including acylguanidine compounds, and methods of treatment and pharmaceutical compositions that utilize or comprise one or more such compounds. Compounds of the invention are particularly useful for the treatment or prophylaxis of neurological injury and neurodegenerative disorders.

2. Background

Nerve cell death (degeneration) can cause potentially devastating and irreversible effects for an individual and may occur e.g. as a result of stroke, heart attack or other brain or spinal chord ischemia or trauma. Additionally, neurodegenerative disorders involve nerve cell death (degeneration) such as Alzheimer's disease, Parkinson's disease, Huntington's disease, Amyotrophic Lateral Sclerosis, Down's Syndrome and Korsakoff's disease.

Therapies have been investigated to treat nerve cell degeneration and related disorders, e.g., by limiting the extent of nerve cell death that may otherwise occur to an individual. See, e.g., N. L. Reddy et al., *J. Med. Chem.*, 37:260–267 (1994); and WO 95/20950.

The compound MK-801 has exhibited good results in a variety of in vivo models of stroke. See B. Meldrum, *Cerbrovascular Brain Metab. Rev.*, 2:27–57 (1990); D. Choi, *Cerbrovascular Brain Metab. Rev.*, 2:105–147 (1990). See also Merck Index, monograph 3392, 11th ed., 1989. For example, MK-801 exhibits good activity in mouse audiogenic tests, a recognized model for evaluation of neuroprotective drugs. See, e.g., M. Tricklebank et al., *European Journal of Pharmacology*, 167:127–135 (1989); T. Seyfried, *Federation Proceedings*, 38(10):2399–2404 (1979).

However, MK-801 also has shown toxicity and further clinical development of the compound is currently uncertain. See J. W. Olney et al., *Science*, 244:1360–1362 (1989); W. Koek et al., *J. Pharmacol. Exp. Ther.*, 252:349–357 (1990); F. R. Sharp et al., *Society for Neuroscience Abstr.*, abstr. no. 482.3 (1992).

It thus would be highly desirable to have new neuroprotective agents, particularly agents to limit the extent or otherwise treat nerve cell death (degeneration) such as may occur with stroke, heart attack or brain or spinal cord trauma, or to treat neurodegenerative disorders such as Alzheimer's disease, Parkinson's disease, Huntington's disease, Amyotrophic Lateral Sclerosis, Down's Syndrome and Korsakoff's disease.

SUMMARY OF THE INVENTION

In a first aspect, the present invention provides acylguanidine compounds of the following Formula I:

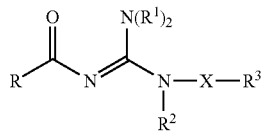

I wherein R is an optionally substituted cyclic alkyl preferably having five or more carbon ring members; optionally substituted carbocyclic aryl having at least about 6 ring carbon atoms; optionally substituted alkylaryl preferably having from 7 to about 18 carbon atoms; or optionally substituted heteroaromatic or heteroalicyclic group having from 1 to 3 rings, 3 to 8 ring members in each ring and from 1 to 3 hetero atoms;

each $R^1$ and $R^2$ are each independently hydrogen, optionally substituted alkyl preferably having from 1 to about 20 carbon atoms, more preferably 1 to about 8 carbon atoms, still more preferably 1 to about 3 carbon atoms; optionally substituted alkenyl preferably having 2 to about 20 carbon atoms, more preferably 2 to about 8 carbon atoms; optionally substituted alkynyl preferably having 2 to about 20 carbon atoms, more preferably 2 to about 8 carbon atoms; optionally substituted alkoxy preferably having from 1 to about 20 carbon atoms, more preferably 1 to about 8 carbon atoms, still more preferably 1 to about 3 carbon atoms; optionally substituted alkylthio preferably having from 1 to about 20 carbon atoms, more preferably 1 to about 8 carbon atoms, still more preferably 1 to about 3 carbon atoms; optionally substituted alkylsulfinyl preferably having from 1 to about 20 carbon atoms, more preferably 1 to about 8 carbon atoms, still more preferably 1 to about 3 carbon atoms; optionally substituted alkylsulfonyl preferably having from 1 to about 20 carbon atoms, more preferably 1 to about 8 carbon atoms, still more preferably 1 to about 3 carbon atoms; optionally substituted carbocyclic aryl having at least about 6 ring carbon atoms; or optionally substituted heteroaromatic or heteroalicyclic group having from 1 to 3 hetero atoms;

X is a chemical bond; optionally substituted alkylene, alkenylene or alkenylene linkage preferably having from 1 to about 6 carbons in the linkage, more preferably from 1 to 4 carbons in the linkage; or an optionally substituted heteroalkylene, heteroalkenylene heteroalkynylene linkage preferably having from 1 to about 6 carbons in the linkage, more preferably from 1 to 4 carbons in the linkage; and $R^3$ is an optionally substituted cycloalkyl preferably having 3 or more carbon ring members, more preferably about 5 or more carbon ring members; optionally substituted carbocyclic aryl having at least about 6 ring carbon atoms; optionally substituted alkylaryl preferably having from 7 to about 18 carbon atoms; or optionally substituted heteroaromatic or heteroalicyclic group having from 1 to 3 rings, 3 to 8 ring members in each ring and from 1 to 3 hetero atoms; and pharmaceutically acceptable salts thereof.

In the above Formula I, X may suitably be a chemical bond, i.e. compounds of the following Formula IA:

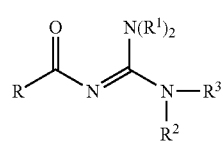

IA wherein R, $R^1$, $R^2$ and $R^3$ are each the same as defined above for Formula I; and pharmaceutically acceptable salts of those compounds.

It also has been found that compounds having X being an alkylene linkage, particularly $C_{1-4}$ alkylene, exhibit significant biological activity as shown in the examples which follow. Thus preferred are compounds of the following Formula IB:

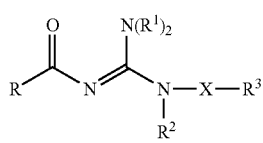

IB wherein X is an optionally substituted alkylene linkage preferably having from 1 to about 6 carbon atoms in the alkylene chain, more preferably 1 to 4 carbon atoms in the alkylene chain, and R, $R^1$, $R^2$ and $R^3$ are each the same as defined above for Formula I; and pharmaceutically acceptable salts of those compounds.

Preferred compounds also include those of the above Formulae I, IA or IB wherein one or more of each $R^1$ and $R^2$ are hydrogen, including wherein each $R^1$ and $R^2$ are all hydrogen. Generally preferred $R^2$ groups of Formulae I, IA and IB include hydrogen and optionally substituted alkyl such as optionally substituted $C_{1-6}$ alkyl, or more preferably optionally substituted $C_{1-3}$ alkyl. Preferred $R^3$ groups of Formula I, IA and IB include optionally substituted carbocyclic aryl or alkaryl such as optionally substituted phenyl, naphthyl and the like, and optionally substituted heteroalicyclic or heteroaromatic such as indolyl and the like, or optionally substituted cycloalkyl such as cyclohexyl and the like.

In a further aspect, the invention provides acylimine-substituted indolinyl-type compounds, particularly compounds of the following Formula II:

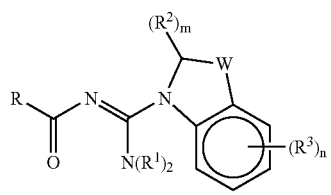

II wherein R is an optionally substituted cyclic alkyl preferably having five or more carbon ring members; optionally substituted carbocyclic aryl having at least about 6 ring carbon atoms; optionally substituted alkylaryl preferably having from 7 to about 18 carbon atoms; or optionally substituted heteroaromatic or heteroalicyclic group having from 1 to 3 rings, 3 to 8 ring members in each ring and from 1 to 3 hetero atoms;

$R^1$ is the selected from the same group defined for $R^1$ and $R^2$ in Formula I;

each $R^2$ and each $R^3$ (i.e. substituent of the 4, 5, 6 and 7 aromatic ring positions) are each independently hydrogen, halogen, hydroxyl, azido, optionally substituted alkyl preferably having from 1 to about 20 carbon atoms, optionally substituted alkenyl preferably having from 2 to about 20 carbon atoms, optionally substituted alkynyl preferably having from 2 to about 20 carbon atoms, optionally substituted alkoxy preferably having from 1 to about 20 carbon atoms, optionally substituted alkylthio preferably having 1 to about 20 carbon atoms, optionally substituted alkylsulfinyl preferably having from 1 to about 20 carbon atoms, optionally substituted alkylsulfonyl preferably having from 1 to about 20 carbon atoms, optionally substituted aminoalkyl preferably having from 1 to about 20 carbon atoms, optionally substituted carbocyclic aryl having at least about 6 ring carbon atoms, or optionally substituted aralkyl having at least about 6 ring carbon atoms;

W is optionally substituted methylene (—$CH_2$—; i.e. indolinyl compounds), —S— (i.e. 3-benzothiazolinylcarboximidamide compounds), —O—, optionally substituted —N—, —S(O)— or —$S(O_2)$—;

m is 0, 1 or 2; n is 0, 1, 2, 3 or 4; and pharmaceutically acceptable salts of those compounds.

In Formula II, generally preferred are compounds where W is optionally substituted methylene, i.e. indolinyl compounds. Optionally substituted phenyl, naphthyl, adamantyl and thiophenyl and other heteroaromatic groups are preferred R groups for compounds of Formula II. Preferred compounds of Formula II also include those where $R^1$ is hydrogen.

In a yet further aspect, the invention provides acylimine-substituted tetrahydroquinolinyl-type compounds, particularly compounds of the following Formula III:

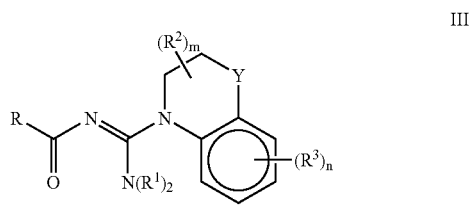

III wherein R is an optionally substituted cyclic alkyl preferably having five or more carbon ring members; optionally substituted carbocyclic aryl having at least about 6 ring carbon atoms; optionally substituted alkylaryl preferably having from 7 to about 18 carbon atoms; or an optionally substituted heteroaromatic or heteroalicyclic group having from 1 to 3 rings, 3 to 8 ring members in each ring and from 1 to 3 hetero atoms;

each $R^1$ is selected from the same group as defined for $R^1$ and $R^2$ in Formula I above;

each $R^2$ (i.e. substituent of the 2 and 3 ring positions) and each $R^3$ (i.e. substituent of the 5, 6, 7 and 8 aromatic ring positions) are each independently hydrogen, halogen, hydroxyl, azido, optionally substituted alkyl preferably having from 1 to about 20 carbon atoms, optionally substituted alkenyl preferably having from 2 to about 20 carbon atoms, optionally substituted alkynyl preferably having from 2 to about 20 carbon atoms, optionally substituted alkoxy preferably having from 1 to about 20 carbon atoms, optionally substituted alkylthio preferably having 1 to about 20 carbon atoms, optionally substituted alkylsulfinyl preferably having from 1 to about 20 carbon atoms, optionally substituted alkylsulfonyl preferably having from 1 to about 20 carbon atoms, optionally substituted aminoalkyl preferably having from 1 to about 20 carbon atoms, optionally substituted carbocyclic aryl having at least about 6 ring carbon atoms, or optionally substituted aralkyl having at least about 6 ring carbon atoms;

Y is optionally substituted methylene (—$CH_2$—, i.e. 1,2,3,4-tetrahydroquinolinyl compounds), —O— (i.e. 2,3- benzmorpholinyl compounds), —S— (i.e. 2,3-benzthiomorpholinyl compounds), —S(O)—, —S(O$_2$)—, or optionally substituted —N—, m and n are each independently 0 (i.e. the available ring are each hydrogen-substituted), 1, 2, 3 or 4; and pharmaceutically acceptable salts of those compounds.

In Formula III, generally preferred are compounds where Y is methylene, i.e. 1,2,3,4-tetrahydroquinolinyl compounds. Optionally substituted phenyl and naphthyl are preferred R groups for compounds of Formula III. Preferred compounds of Formula III also include those where R$^1$ is hydrogen.

In a further aspect, the invention provide acylimine-substituted tetrahydroisoquinolinyl compounds, particularly compounds of the following Formula IV:

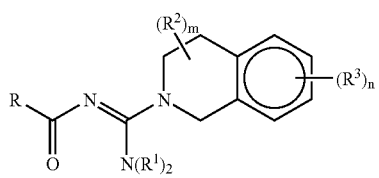

IV wherein R and each R$^1$ are the same as defined above for Formula I;

each R$^2$ (i.e. substituent of the 1, 3 and 4 tetrahydroisoquinolinyl ring positions) and each R$^3$ (i.e. substituent of the 5, 6, 7 and 8 tetrahydroisoquinolinyl ring positions) are each independently hydrogen, halogen, hydroxyl, azido, optionally substituted alkyl preferably having from 1 to about 20 carbon atoms, optionally substituted alkenyl preferably having from 2 to about 20 carbon atoms, optionally substituted alkynyl preferably having from 2 to about 20 carbon atoms, optionally substituted alkoxy preferably having from 1 to about 20 carbon atoms, optionally substituted alkylthio preferably having 1 to about 20 carbon atoms, optionally substituted alkylsulfinyl preferably having from 1 to about 20 carbon atoms, optionally substituted alkylsulfonyl preferably having from 1 to about 20 carbon atoms, optionally substituted aminoalkyl preferably having from 1 to about 20 carbon atoms, optionally substituted carbocyclic aryl suitably at least about 6 ring carbon atoms, or optionally substituted aralkyl suitably having at least about 6 ring carbon atoms;

m is 0 (i.e. the 1, 3 and 4 tetrahydroisoquinolinyl ring positions are each hydrogen-substituted), 1, 2, 3, 4, 5 or 6; n is 0 (i.e. the 5, 6, 7 and 8 tetrahydroisoquinolinyl ring positions are each hydrogen-substituted), 1, 2, 3 or 4; and pharmaceutically acceptable salts thereof.

In another aspect, the invention provides compounds of the following Formula V:

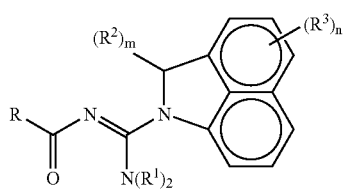

V wherein R and each R$^1$ are the same as defined above for Formula I;

each R$^2$ and each R$^3$ (i.e. substituent of the aromatic positions 3–8) are each independently hydrogen, halogen, hydroxyl, azido, optionally substituted alkyl preferably having from 1 to about 20 carbon atoms, optionally substituted alkenyl preferably having from 2 to about 20 carbon atoms, optionally substituted alkynyl preferably having from 2 to about 20 carbon atoms, optionally substituted alkoxy preferably having from 1 to about 20 carbon atoms, optionally substituted alkylthio preferably having 1 to about 20 carbon atoms, optionally substituted alkylsulfinyl preferably having from 1 to about 20 carbon atoms, optionally substituted alkylsulfonyl preferably having from 1 to about 20 carbon atoms, optionally substituted aminoalkyl preferably having from 1 to about 20 carbon atoms, optionally substituted carbocyclic aryl suitably having at least about 6 ring carbon atoms, or optionally substituted aralkyl suitably having at least about 6 ring carbon atoms;

m is 0 (i.e. the 2-benz[cd]indolinyl position is hydrogen-substituted), 1 or 2; and n is 0 (i.e. the available ring are each hydrogen-substituted), 1, 2, 3, 4, 5 or 6; and pharmaceutically acceptable salts thereof.

Still further, the invention provides compounds of the following Formula VI:

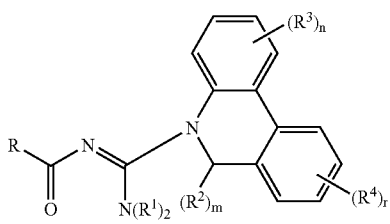

VI wherein R and each R$^1$ are the same as defined above for Formula I;

each R$^2$, each R$^3$ (i.e. substituent of the aromatic positions 1–4) and each R$^4$ (i.e. substituent of the aromatic positions 7–10) are each independently hydrogen, halogen, hydroxyl, azido, optionally substituted alkyl preferably having from 1 to about 20 carbon atoms, optionally substituted alkenyl preferably having from 2 to about 20 carbon atoms, optionally substituted alkynyl preferably having from 2 to about 20 carbon atoms, optionally substituted alkoxy preferably having from 1 to about 20 carbon atoms, optionally substituted alkylthio preferably having 1 to about 20 carbon atoms, optionally substituted alkylsulfinyl preferably having from 1 to about 20 carbon atoms, optionally substituted alkylsulfonyl preferably having from 1 to about 20 carbon atoms, optionally substituted aminoalkyl preferably having from 1 to about 20 carbon atoms, optionally substituted carbocyclic aryl suitably having at least about 6 ring carbon atoms, or optionally substituted aralkyl suitably having at least about 6 ring carbon atoms;

m is 0 (i.e. the 5,6-dihydrophenanthridinyl ring position is hydrogen-substituted), 1 or 2; and n and r are each independently 0 (i.e. the ring positions are each hydrogen-substituted), 1, 2, 3 or 4; and pharmaceutically acceptable salts thereof.

In an additional aspect, the invention provides compounds of the following Formula VII:

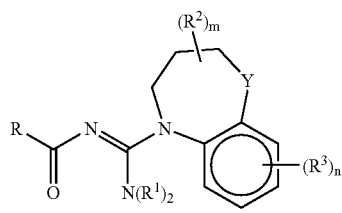

wherein R, each $R^1$, Y, each $R^2$, each $R^3$ and n are the same as defined above for Formula III; and m of Formula VII is an integer equal to 0–6, and preferably m is 0, 1 or 2; and pharmaceutically acceptable salts thereof.

The invention also provides compounds of the following Formula VIII:

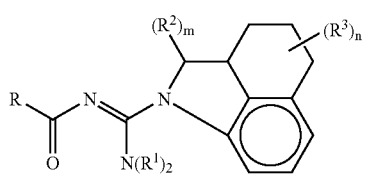

wherein R, each $R^1$, each $R^2$, each $R^3$ and m are the same as defined above for Formula V; and n of Formula VIII is an integer equal to 0–9, and preferably n is 0, 1 or 2; and pharmaceutically acceptable salts thereof. It is understand that each $R^3$ can be the same or different and may be present on either the non-aromatic or aromatic fused ring as depicted in the above structural formula.

The invention further provides compounds of the following Formula IX:

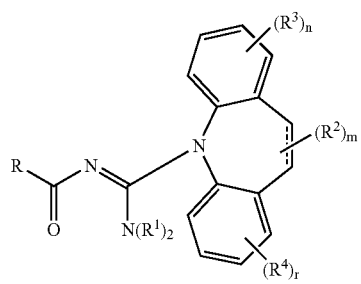

wherein R, $R^1$, $R^2$, $R^3$, n and r are the same as defined above for Formula VI, and m of Formula IX is an integer equal to 0–4, and preferably m is 0, 1 or 2, and the dotted line in Formula IX represents an optional carbon—carbon double bond (endocyclic bond); and pharmaceutically acceptable salts thereof.

In a further aspect, compounds of the following Formula X are provided:

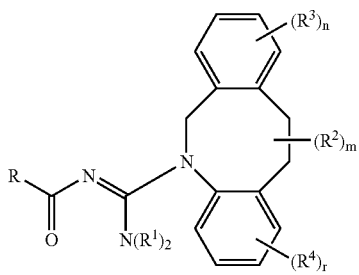

wherein R, $R^1$, $R^2$, $R^3$, n and r are the same as defined above for Formula VI, and m of Formula X is an integer equal to 0–6 (i.e. $R^2$ may be a substituent at any of the available three saturated ring positions), and preferably m is 0, 1 or 2; and pharmaceutically acceptable salts thereof.

In a further aspect, the invention also provides compounds of the Formulae I', IA', IB', II', III', IV', V', VI', VII', VIII', IX' and X', which formulae are defined the same as Formulae I, IA, IB, II, III, IV, V, VI, VII, VIII, IX and X respectively, except that the substituent R may be selected from the group of an optionally substituted cyclic alkyl preferably having five or more carbon ring members; optionally substituted carbocyclic aryl having at least about 6 ring carbon atoms; optionally substituted alkylaryl preferably having from 7 to about 18 carbon atoms; or optionally substituted heteroaromatic or heteroalicyclic group having from 1 to 3 rings, 3 to 8 ring members in each ring and from 1 to 3 hetero (N, O or S) atoms; optionally substituted aralkyl preferably having from 7 to about 18 carbon atoms; optionally substituted heteroaralkyl preferably having from 5 to about 18 carbon atoms, and from 1 to 3 rings, 3 to 8 ring members in each ring and from 1 to 3 hetero (N, O or S) atoms; or optionally substituted heteroalicyclicalkyl preferably having from 5 to about 18 carbon atoms, and from 1 to 3 rings, 3 to 8 ring members in each ring and from 1 to 3 hetero (N, O or S) atoms. For such compounds of Formulae I', IA', IB', II', III', IV', V', VI', VII', VIII', IX' and X', preferred R groups include optionally substituted aralkyl, particularly optionally substituted carbocyclic aralkyl such as optionally substituted phenalkyl, e.g. optionally substituted phenyl($C_{1-8}$)alkyl, more typically optionally substituted phenyl($C_{1-6}$)alkyl, still more typically optionally substituted phenyl($C_{1-4}$)alkyl such as an optionally substituted phenacetyl ($C_6H_5CH_2C(=O)$) group and the like. Additional particularly suitable R groups of such compounds of Formulae I', IA', IB', II', III', IV', V', VI', VII', VIII', IX' and X' include optionally substituted heteroaryalkyl and optionally substituted heteroalicyclicalkyl, such as optionally substituted heteroaryl($C_{1-8}$)alkyl or heteroalicyclic($C_{1-8}$)alkyl, more typically optionally substituted heteroaryl($C_{1-6}$)alkyl or heteroalicyclic($C_{1-6}$)alkyl, still more typically optionally substituted heteroaryl($C_{1-4}$)alkyl or heteroalicyclic($C_{1-4}$)alkyl. It also should be understood that preferred substituents as disclosed herein of compounds of Formula I, IA, IB, II, III, IV, V, VI, VII, VIII, IX and X are also preferred substituents of the corresponding Formulae I', IA', IB', II', III', IV', V', VI', VII', VIII', IX' and X', unless indicated otherwise.

Compounds of the invention (i.e. compounds of Formulae I, IA, IB, II, III, IV, V, VI, VII, VIII, IX and X as well as compounds of Formulae I', IA', IB', II', III', IV', V', VI', VII', VIII', IX' and X') are useful for a number of therapeutic applications. In particular, the invention includes methods for treatment and/or prophylaxis of neurological conditions/injuries such as epilepsy, neurodegenerative conditions and/or nerve cell death (degeneration) resulting from or associated with e.g. hypoxia, hypoglycemia, brain or spinal chord ischemia, retinal ischemia, brain or spinal chord trauma or post-surgical neurological deficits and the like as well as neuropathic pain. The invention also includes methods for treating peripheral necropathy. The compounds of the invention are especially useful for treatment of a person susceptible or suffering from stroke or heart attack or neurological deficits relating to cardiac arrest, a person suffering or susceptible to brain or spinal cord injury, or a person suffering from the effects of retinal ischemica or degeneration, or a person suffering from decreased blood flow or nutrient supply to retinal tissue or optic nerve, retinal trauma, glaucoma or optic nerve injury. Compounds of the invention also are useful to treat and/or prevent various neurodegenerative diseases such as Parkinson's disease, Huntington's disease, Amyotrophic Lateral Sclerosis, Alzheimer's disease, Down's Syndrome, Korsakoff's disease, cerebral palsy and/or age-dependent dementia. Compounds of the invention will be further useful to treat and/or prevent migraines, shingles (herpes zoster), epilepsy, emesis and/or narcotic withdrawal symptoms. Compounds of the invention will be useful for treatment of various types of pain, including e.g. chronic pain. The treatment methods of the invention in general comprise administration of a therapeutically effective amount of one or more compounds of the invention to an animal, including a mammal, particularly a human. Particularly preferred compounds of the invention exhibit good activity in an anticonvulsant in vivo mouse audiogenic assay e.g. as disclosed in Example 11 which follows, preferably about 20% or more inhibition at a dose of a compound of the invention of 20 mg/kg, more preferably about 50% or more inhibition at a dose of 20 mg/kg in such an anticonvulsant in vivo audiogenic assay.

The invention also provides pharmaceutical compositions that comprise one or more compounds of the invention and a suitable carrier for the compositions.

Other aspects of the invention are disclosed infra.

DETAILED DESCRIPTION OF THE INVENTION

We have now discovered that compounds of the above-defined Formulae I (which includes Formulae IA and IB), II, III, IV, V, VI, VII, VIII, IX and X as well as Formulae I', IA', IB', II', III', IV', V', VI', VII', VIII', IX' and X') are useful for therapeutic applications, including to treat neurological injury or a neurodegenerative disorder.

Suitable halogen substituent groups of compounds of Formulae I, IA, IB, II, III, IV, V, VI, VII, VIII, IX and X as well as Formulae I', IA', IB', II', III', IV', V', VI', VII', VIII', IX' and X''' as defined above (i.e. compounds of the invention) include F, Cl, Br and I. Alkyl groups of compounds of the invention typically have from 1 to about 12 carbon atoms, more preferably 1 to about 8 carbon atoms, still more preferably 1 to about 6 carbon atoms, even more preferably 1, 2, 3 or 4 carbon atoms, or still more preferably 1, 2 or 3 carbon atoms. As used herein, the term alkyl unless otherwise modified refers to both cyclic and noncyclic groups, although of course cyclic groups will comprise at least three carbon ring members. Preferred alkenyl and alkynyl groups of compounds of the invention have one or more unsaturated linkages and typically from 2 to about 12 carbon atoms, more preferably 2 to about 8 carbon atoms, still more preferably 2 to about 6 carbon atoms, even more preferably 1, 2, 3 or 4 carbon atoms. The terms alkenyl and alkynyl as used herein refer to both cyclic and noncyclic groups, although straight or branched noncyclic groups are generally more preferred. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. Preferred alkylthio groups of compounds of the invention include those groups having one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred. Preferred alkylsulfinyl groups of compounds of the invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties. Suitable heteroaromatic groups of compounds of the invention contain one or more N, O or S atoms and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazol. Suitable heteroalicyclic groups of compounds of the invention contain one or more N, O or S atoms and include, e.g., tetrahydrofuranyl, thienyl, tetrahydropyranyl, piperidinyl, morpholino and pyrrolindinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl. Substituted carbocyclic groups are particularly suitable including substituted phenyl, such as 2-substituted phenyl, 3-substituted phenyl, 4-substituted phenyl, 2,3-substituted phenyl, 2,5-substituted phenyl, 2,3,5-substituted and 2,4,5-substituted phenyl; and substituted naphthyl, including naphthyl substituted at the 5, 6 and/or 7 positions. Preferred substituents of such substituted carbocyclic groups are identified below.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms.

Preferred aralkyl groups include benzyl and methylenenaphthyl (—CH$_2$-naphthyl), and other carbocyclic aralkyl groups, as discussed above.

Suitable heteroaralkyl groups of compounds of the invention include single and multiple ring compounds, including multiple ring compounds that contain separate and/or fused heteroaryl groups, where such groups are substituted onto an alkyl linkage. More preferably, a heteroaralkyl group contains a heteroaryl group that has 1 to 3 rings, 3 to 8 ring members in each ring and from 1 to 3 hetero (N, O or S) atoms, substituted onto an alkyl linkage. Suitable heteroaryl groups substituted onto an alkyl linkage include e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazol, as well as such groups fused to one or more benzene rings.

Suitable heteroalicyclicalkyl groups of compounds of the invention include single and multiple ring compounds, where such groups are substituted onto an alkyl linkage. More preferably, a heteroalicralkyl group contains at least one ring that has 3 to 8 ring members from 1 to 3 hetero (N, O or S) atoms, substituted onto an alkyl linkage. Suitable heteroalicyclic groups substituted onto an alkyl linkage include e.g. tetrahydrofuranyl, thienyl, tetrahydropyranyl, piperidinyl, morpholino and pyrrolindinyl groups.

As discussed above, X groups of Formula I and I' suitably are alkylene or heteroalkylene linkages, or may contain one or more carbon—carbon double or triple bonds, i.e. alkenylene, alkynylene, heteroalkenylene or heteroalkynylene linkage. Such unsaturated X groups typically contain 1, 2, 3 or 4 carbon—carbon multiple bonds, more typically 1 or 2 carbon—carbon multiple bonds. An X group that is heteroalkylene, heteroalkenylene or heteroalkynylene contains one or more N, O or S atoms in the chain between amino group and R$^3$ group of Formula I or I', with other atoms in the chain suitably being carbons. Typically a heteroalkylene, heteroalkenylene or heteroalkynylene X group contains 1–3 N, O or S atoms in the chain, more typically 1 or 2 N, O or S atoms. Typically an X group contains from about 1 to 6 carbon atoms.

Suitable cyclic alkyl R groups of Formulae I–X and I'–X' and R$^3$ groups of Formulae I, IA, IB, I', IA' and IB' include groups having five or six or more ring carbon atoms, particularly optionally substituted adamanyl, isobornyl, norbornyl, cyclohexyl, cyclopentyl and the like. Generally preferred cyclic alkyl groups have from 5 to about 10 ring members. Cyclic alkyl groups having bridged structures, such as adamantyl, are particularly preferred.

Generally preferred R$^1$ groups of Formulae I through X and I' through X' include hydrogen and alkyl such as C$_{1-6}$ alkyl, more preferably alkyl having 1, 2 or 3 carbon atoms. Suitable compounds also include those where both R$^1$ of a compound are hydrogen, or where at least one R$^1$ group is hydrogen.

As discussed above, R, R$^1$, X, R$^2$, R$^3$, R$^4$, X, Y and W groups of compound of the invention are optionally substituted. A "substituted" R, R$^1$, X, R$^2$, R$^3$, R$^4$, X, Y and W group or other substituent may be substituted at one or more available positions, typically 1 to 3 or 4 positions, by one or more suitable groups such as those disclosed herein. Suitable groups that may be present on a "substituted" R, R$^1$, X, R$^2$, R$^3$, R$^4$, Y and W group or other substituent include e.g. halogen such as fluoro, chloro, bromo and iodo; cyano; hydroxyl; nitro; azido; alkanoyl such as a C$_{1-6}$ alkanoyl group such as acyl and the like; carboxamido; alkyl groups including those groups having 1 to about 12 carbon atoms or from 1 to about 6 carbon atoms and more preferably 1–3 carbon atoms; alkenyl and alkynyl groups including groups having one or more unsaturated linkages and from 2 to about 12 carbon or from 2 to about 6 carbon atoms; alkoxy groups having those having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocyclic aryl having 6 or more carbons, particularly phenyl (e.g. an R group being a substituted or unsubstituted biphenyl moiety); and aralkyl such as benzyl.

Generally preferred substituents of "substituted" nitrogen and methylene W and Y groups of compounds of Formulae II, III, VII, II', III', and VII' include substituted and unsubstituted alkyl, including C$_{1-4}$ alkyl and halo-substituted C$_{1-4}$ alkyl, particularly fluoro-substituted C$_{1-4}$ alkyl such as trifluoromethyl, and in the case of a substituted methylene group, halogen and alkylthio.

Preferred carbocyclic ring substituents of compounds of the invention include halogen (F, Cl, Br and I; hydroxyl; azido; optionally substituted alkyl having 1 to about 6 carbons such as methyl, ethyl, propyl and butyl and branched groups such as isopropyl, sec-butyl and tert-butyl, and including halogenated alkyl, particularly fluoro-alkyl having 1 to about 6 carbon atoms; optionally substituted alkoxy having 1 to about 6 carbons such as methoxy, ethoxy, propoxy and butoxy, and including halogenated alkoxy, particularly fluoro-alkoxy having 1 to about 6 carbon atoms; optionally substituted alkylthio having 1 to about 6 carbons such as methylthio and ethylthio; optionally substituted alkylsulfinyl having 1 to about 6 carbons such as methylsulfinyl (—S(O)CH$_3$) and ethylsulfinyl (—S(O)CH$_2$CH$_3$); optionally substituted alkylsulfonyl having 1 to about 6 carbons such as methylsulfonyl (—S(O)$_2$CH$_3$) and ethylsulfonyl (—S(O)$_2$CH$_2$CH$_3$); and optionally substituted arylalkoxy such as benzyloxy (C$_6$H$_5$CH$_2$O—).

It should be understood that alkoxy, alkylthio, alkylsulfinyl, alkylsulfonyl and aminoalkyl substituent groups described above include groups where a hetero atom is directly bonded to a ring system, such as a carbocyclic aryl group or a heterocyclic group, as well as groups where a hetero atom of the group is spaced from such ring system by an alkylene linkage, e.g. of 1 to about 4 carbon atoms.

Also, in the above Formulae I through X and I' through X', additional preferred groups that may be R$^2$, R$^3$ and R$^4$ as those substituent groups are defined above, include optionally substituted sulfonamide, optionally substituted urea and optionally substituted thioamide.

Without wishing to be bound by theory, compounds of the invention that contain an alkylsulfinyl and/or alkylsulfonyl group, may be, in effect, "pro-drugs" wherein after administration of the compound to a subject the sulfinyl or sulfonyl group(s) are metabolized (reduced) in vivo to the corresponding sulfide moiety.

Specifically preferred compounds of the invention include the following:

N-(4-methylbenzoyl)-N'-methyl-N'-(3-methylthiophenyl) guanidine;

N-(4-methylbenzoyl)-N'-methyl-N'-(3-iodophenylmethyl) guanidine;
N-(4-methylbenzoyl)-N'-(1-naphthyl)guanidine;
N-(4-methylbenzoyl)-N'-(4-benzyloxyphenyl)guanidine;
N-(4-methylbenzoyl)-N'-(4-tertbutylphenyl)guanidine;
N-(4-methylbenzoyl)-1-indolinylcarboximidamide;
N-(4-methylbenzoyl)-N'-(4-isopropylphenyl)guanidine;
N-(4-methylbenzoyl)-1-[7-(trifluoromethyl)-1,2,3,4-tetrahydroquinoline]carboximidamide;
N-(4-methylbenzoyl)-1-(1,2,3,4-tetrahydroquinoline) carboximidamide;
N-(4-methylbenzoyl)-N'-(2,5-dibromophenyl)guanidine;
N-(4-methylbenzoyl)-N'-(4-isopropoxyphenyl)guanidine;
N-(4-methylbenzoyl)-N'-(3,4,5-trimethoxyphenyl)guanidine;
N-(4-methylbenzoyl)-N'-(2-isopropylphenyl)guanidine;
N-(2,5-dichlorobenzoyl)-N'-methyl-N'-(3-iodophenyl) guanidine;
N-(2,5-dichlorobenzoyl)-N'-methyl-N'-(3-methylthiophenyl)guanidine;
N-(2,5-dichlorobenzoyl)-N'-(1-naphthyl)guanidine;
N-(2,5-dichlorobenzoyl)-N'-(4-benzyloxyphenyl)guanidine;
N-(2,5-dichlorobenzoyl)-N'-(4-isopropylphenyl)guanidine;
N-(2,5-dichlorobenzoyl)-N'-(4-tertbutylphenyl)guanidine;
N-(2,5-dichlorobenzoyl)-1-indolinylcarboximidamide;
N-(2,5-dichlorobenzoyl)-N'-methyl-N'-(4-isopropylphenyl) guanidine;
N-(phenylacetyl)-N'-(4-benzyloxyphenyl)guanidine;
N-(phenylacetyl)-N'-(4-isopropylphenyl)guanidine;
N-(phenylacetyl)-N'-(4-tert-butylphenyl)guanidine;
N-(phenylacetyl)-1-indolinylcarboximidamide;
N-(phenylacetyl)-1-(1,2,3,4-tetrahydroquinoline)carboximidamide;
N-(phenylacetyl)-N'-(4-isopropoxyphenyl)guanidine;
N-(phenylacetyl)-N'-(4-isopropylphenyl)-N'-methylguanidine;
N-(adamantan-1-carbonyl)-N'-methyl-N'-(3-iodophenyl) guanidine;
N-(adamantan-1-carbonyl)-N'-(1-naphthyl)guanidine;
N-(adamantan-1-carbonyl)-N'-(4-benzyloxyphenyl)guanidine;
N-(adamantan-1-carbonyl)-N'-(4-isopropylphenyl)guanidine;
N-(adamantan-1-carbonyl)-N'-(4-tert-butylphenyl)guanidine;
N-(adamantan-1-carbonyl)-1-(indolinyl)carboximidamide;
N-(adamantan-1-carbonyl)-1-(1,2,3,4-tetrahydroquinolinyl) carboximidamide;
N-(adamantan-1-carbonyl)-N'-(2,5-dibromophenyl)guanidine;
N-(adamantan-1-carbonyl)-N'-(4-isopropylphenyl)-N'-methyl)guanidine;
N-(4-chlorobenzoyl)-N'-methyl-N'-(3-iodophenyl)guanidine;
N-(4-chlorobenzoyl)-N'-methyl-N'-(3-methylthiophenyl) guanidine;
N-(4-chlorobenzoyl)-N'-(1-naphthyl)guanidine;
N-(4-chlorobenzoyl)-N'-(4-benzyloxyphenyl)guanidine;
N-(4-chlorobenzoyl)-N'-(4-isopropylphenyl)guanidine;
N-(4-chlorobenzoyl)-N'-(4-tert-butylphenyl)guanidine;
N-(4-chlorobenzoyl)-1-(indolinyl) carboximidamide;
N-(4-chlorobenzoyl)-1-(1,2,3,4-tetrahydroquinolinyl)carboximidamide;
N-(4-chlorobenzoyl)-N'-(2,5-dibromophenyl)guanidine;
N-(3,4-dichlorobenzoyl)-N'-methyl-N'-(3-iodophenyl) guanidine;
N-(3,4-dichlorobenzoyl)-N'-(1-naphthyl)guanidine;
N-(3,4-dichlorobenzoyl)-N'-(4-benzyloxyphenyl)guanidine;
N-(3,4-dichlorobenzoyl)-N'-(4-isopropylphenyl)guanidine;
N-(3,4-dichlorobenzoyl)-N'-(4-tert-butylphenyl)guanidine;
N-(3,4-dichlorobenzoyl)-1-(indolinyl)carboximidamide;
N-(3,4-dichlorobenzoyl)-1-(1,2,3,4-tetrahydroquinolinyl) carboximidamide;
N-(3,4-dichlorobenzoyl)-N'-methyl-N'-(4-isopropylphenyl) guanidine;
N-(thiophen-2-carbonyl)-N'-methyl-N'-(3-iodophenyl) guanidine;
N-(thiophen-2-carbonyl)-N'-methyl-N'-(3-methylthiophenyl)guanidine;
N-(thiophen-2-carbonyl)-N'-(1-naphthyl)guanidine;
N-(thiophen-2-carbonyl)-N'-(4-benzyloxyphenyl)guanidine;
N-(thiophen-2-carbonyl)-N'-(4-isopropylphenyl)guanidine;
N-(thiophen-2-carbonyl)-N'-(4-tert-butylphenyl)guanidine;
N-(thiophen-2-carbonyl)-1-(indolinyl)carboximidamide;
N-(thiophen-2-carbonyl)-1-(1,2,3,4-tetrahydroquinolinyl) carboximidamide;
N-(thiophen-2-carbonyl)-N'-methyl-N'-(4-isopropylphenyl) guanidine;
N-(furan-2-carbonyl)-N'-methyl-N'-(3-iodophenyl)guanidine;
N-(furan-2-carbonyl)-N'-methyl-N'-(3-methylthiophenyl) guanidine;
N-(furan-2-carbonyl)-N'-(1-naphthyl)guanidine;
N-(furan-2-carbonyl)-N'-(4-benzyloxyphenyl)guanidine;
N-(furan-2-carbonyl)-N'-(4-isopropylphenyl)guanidine;
N-(furan-2-carbonyl)-N'-(4-tert-butylphenyl)guanidine;
N-(furan-2-carbonyl)-1-(indolinyl)carboximidamide;
N-(furan-2-carbonyl)-1-(1,2,3,4-tetrahydroquinolinyl)carboximidamide;
N-(furan-2-carbonyl)-N'-(4-isopropylphenyl)-N'-methylguanidine;
N-(pyridin-3-carbonyl)-N'-(1-naphthyl)guanidine;
N-(pyridin-3-carbonyl)-N'-(4-benzyloxyphenyl)guanidine;
N-(pyridin-3-carbonyl)-N'-(4-isopropylphenyl)guanidine;
N-(pyridin-3-carbonyl)-N'-(4-tert-butylphenyl)guanidine;
N-(pyridin-3-carbonyl)-1-(indolinyl)carboximidamide;
N-(pyridin-3-carbonyl)-1-(1,2,3,4-tetrahydroquinolinyl)carboximidamide;
N-(4-methoxybenzoyl)-N'-(4-benzyloxyphenyl)guanidine;
N-(4-methoxybenzoyl)-N'-(4-isopropylphenyl)guanidine;
N-(4-methoxybenzoyl)-N'-(4-isopropoxyphenyl)guanidine;
N-(4-methoxybenzoyl)-N'-(3,4,5-trimethoxyphenyl)guanidine;
N-(1-naphthoyl)-N'-(4-benzyloxyphenyl)guanidine;
N-(1-naphthoyl)-N'-(4-isopropylphenyl)guanidine;
N-(1-naphthoyl)-N'-(4-isopropoxyphenyl)guanidine;
N-(3,4,5-trimethoxybenzoyl)-N'-(2-isopropylphenyl)guanidine;
N-(3,4,5-trimethoxybenzoyl)-N'-(4-isopropoxyphenyl) guanidine;
N-(4-butoxybenzoyl)-N'-(2-isopropylphenyl)guanidine;
N-(4-butoxybenzoyl)-N'-(4-isopropoxyphenyl)guanidine;
N-(4-butoxybenzoyl)-N'-(3,4,5-trimethoxyphenyl)guanidine;
N-(4-ethoxybenzoyl)-N'-(2-isopropylphenyl)guanidine;
N-(4-ethoxybenzoyl)-N'-(4-isopropoxyphenyl)guanidine;
N-(4-methylbenzoyl)-N'-(benzyl)guanidine;
N-(4-methylbenzoyl)-N'-(2-phenethyl)guanidine;
N-(4-methylbenzoyl)-N'-(3-dimethylaminopropyl)guanidine;
N-(4-methylbenzoyl)-N'-(4-phenylbutyl)guanidine;
N-(4-methylbenzoyl)-N'-(3-phenylpropyl)guanidine;
N-(4-methylbenzoyl)-N'-(1-naphthylmethyl)guanidine;

N-(4-methylbenzoyl)-N'-(2-(4-chlorophenyl)ethyl)guanidine;
N-(4-methylbenzoyl)-N'-(5-phenylpentyl)guanidine;
N-(4-methylbenzoyl)-N'-(3-phenoxypropyl)guanidine;
N-(3,4-dichlorobenzoyl)-N'-(benzyl)guanidine;
N-(3,4-dichlorobenzoyl)-N'-(3-phenylpropyl)guanidine;
N-(4-chlorobenzoyl)-N'-(benzyl)guanidine;
N-(4-chlorobenzoyl)-N'-(2-phenethyl)guanidine;
N-(4-chlorobenzoyl)-N'-(4-phenylbutyl)guanidine;
N-(4-methoxybenzoyl)-N'-(benzyl)guanidine;
N-(4-methoxybenzoyl)-N'-(3-dimethylaminopropyl)guanidine;
N-(4-methoxybenzoyl)-N'-(2-phenethyl)guanidine;
N-(4-methoxybenzoyl)-N'-(4-phenylbutyl)guanidine;
N-(4-methoxybenzoyl)-N'-(2-(4-chlorophenylethyl)guanidine;
N-(4-methoxybenzoyl)-N'-(1-naphthylmethyl)guanidine;
N-(4-methoxybenzoyl)-N'-(3,4,5-trimethoxybenzyl)guanidine;
N-(4-ethoxybenzoyl)-N'-(4-phenylbutyl)guanidine;
N-(4-ethoxybenzoyl)-N'-(2-phenethyl)guanidine;
N-(4-ethoxybenzoyl)-N'-(2-(4-chlorophenyl)ethyl)guanidine;
N-(4-ethoxybenzoyl)-N'-(3-phenylpropyl)guanidine;
N-(4-ethoxybenzoyl)-N'-(1-naphthylmethyl)guanidine;
N-(4-butoxybenzoyl)-N'-(4-phenylbutyl)guanidine;
N-(4-butoxybenzoyl)-N'-(2-phenethyl)guanidine;
N-(4-butoxybenzoyl)-N'-(2-(4-chlorophenyl)ethyl)guanidine;
N-(4-butoxybenzoyl)-N'-(3-phenylpropyl)guanidine;
N-(4-butoxybenzoyl)-N'-(2-(3-indole)ethyl)guanidine;
N-(3,4,5-trimethoxybenzoyl)-N'-(4-phenylbutyl)guanidine;
N-(3,4,5-trimethoxybenzoyl)-N'-(2-(3-indole)ethyl)guanidine;
N-(3,4,5-trimethoxybenzoyl)-N'-(2-phenylethyl)guanidine;
N-(1-naphthoyl)-N'-(benzyl)guanidine;
N-(1-naphthoyl)-N'-(3-dimethylaminopropyl)guanidine;
N-(1-naphthoyl)-N'-(2-phenylethyl)guanidine;
N-(1-naphthoyl)-N'-(4-phenylbutyl)guanidine;
N-(thiophen-2-carbonyl)-N'-(benzyl)guanidine;
N-(thiophen-2-carbonyl)-N'-(3-dimethylaminopropyl)guanidine;
N-(thiophen-2-carbonyl)-N'-(2-phenylethyl)guanidine;
N-(thiophen-2-carbonyl)-N'-(4-phenylbutyl)guanidine;
N-(4-methylbenzoyl)-N'-(cyclohexyl)-N'-methylguanidine;
N-(4-methylbenzoyl)-N'-(4-phenylbutyl)-N''-methylguanidine;
N-(4-methoxybenzoyl)-N'-(5-phenylpentyl)guanidine;
N-(2-methylbenzoyl)-N'-(4-phenylbutyl)guanidine;
N-(2-methylbenzoyl)-N'-(2-isopropylphenyl)guanidine;
N-(2-methylbenzoyl)-N'-(4-isopropylphenyl)guanidine;
N-(2-methylbenzoyl)-N'-(3-phenylpropyl)guanidine;
N-(4-methoxybenzoyl)-N'-(2-phenoxypropyl)guanidine;
N-(4-butoxybenzoyl)-N'-(5-phenylpentyl)guanidine;
N-(4-methylbenzoyl)-N'-(2-phenoxyethyl)guanidine;
N-(4-methoxybenzoyl)-N'-(2-phenoxyethyl)guanidine;
N-(4-ethoxybenzoyl)-N'-[(2-benzylthio) ethyl]guanidine;
N-(4-ethoxybenzoyl)-N'-(3,4,5-trimethoxyphenyl)guanidine;

and pharmaceutically acceptable salts thereof.

Additional specifically preferred compounds of the invention include the following:
N-(2-methylbenzoyl)-N'-(2-isopropylphenyl)guanidine;
N-(2-methylbenzoyl)-N'-(4-isopropylphenyl)guanidine;
N-(4-ethoxybenzoyl)-N'-(3,4,5-trimethoxyphenyl)guanidine;
N-benzoyl-N'-(4-isopropylphenyl)guanidine;
N-benzoyl-N'-(4-isopropoxyphenyl)guanidine;
N-benzoyl-N'-(4-benzyloxyphenyl)guanidine;
N-benzoyl-N'-(2-isopropylphenyl)guanidine;
N-(2,6-dichlorophenacetyl)-N'-(4-benzyloxyphenyl)guanidine;
N-(2,6-dichlorophenacetyl)-N'-(phenyl)guanidine;
N-(2,6-dichlorophenacetyl)-N'-(4-isopropyl)phenylguanidine;
N-(2,6-dichlorophenacetyl)-1-(indolinyl)carboxamidamide;
N-(2-chlorobenzoyl)-N'-(4-isopropyl)phenylguanidine;
N-(2-chlorobenzoyl)-N'-(4-benzyloxyphenyl)guanidine;
N-(2-chlorobenzoyl)-1-(indolinyl)carboxamidamide;
N-(2,6-dichlorobenzoyl)-N'-(4-benzyloxyphenyl)guanidine;
N-(2,6-dichlorobenzoyl)-N'-(2-isopropylphenyl)guanidine;
N-(2,6-dichlorobenzoyl)-N'-(4-isopropylphenyl)guanidine;
N-(2,6-dichlorobenzoyl)-1-(indolinyl)carboxamidamide;
N-(2,6-dichlorobenzoyl)-N'-(trimethoxyphenyl)guanidine;
N-(2,3-dichlorobenzoyl)-N'-(4-isopropyl)phenylguanidine;
N-(2,3-dichlorobenzoyl)-1-(indolinyl)carboxamidamide;
N-(2,3-dichlorobenzoyl)-N'-(4-benzyloxyphenyl)guanidine;
N-(4-methoxybenzoyl)-N'-(5-phenylpentyl)guanidine;
N-(2-methylbenzoyl)-N'-(4-phenylbutyl)guanidine;
N-(2-methylbenzoyl)-N'-(3-phenylpropyl)guanidine;
N-(4-methoxybenzoyl)-N'-(3-phenoxypropyl)guanidine;
N-(4-butoxybenzoyl)-N'-(4-phenylbutyl)guanidine;
N-(4-methoxybenzoyl)-N'-(3-phenoxyethyl)guanidine;
N-(4-ethoxybenzoyl)-N'-(3-benzylthioethyl)guanidine;
N-benzoyl-N'-(4-phenylbutyl)guanidine;
N-benzoyl-N'-(3-phenoxypropyl)guanidine;
N-benzoyl-N'-(3,4,5-trimethoxybenzyl)guanidine;
N-benzoyl-N'-(2-benzylthioethyl)guanidine;
N-(4-methylbenzoyl)-N'-[(indol-3-yl)-2-ethyl]guanidine;
N-(4-chlorobenzoyl)-N'-[(indol-3-yl)-2-ethyl]guanidine;
N-(1-naphthoyl)-N'-[(indol-3-yl)-2-ethyl]guanidine;
N-(thiophen-2-carbonyl)-N'-[(indol-3-yl)-2-ethyl]guanidine;
N-(4-methylbenzoyl)-N'-butylguanidine;
N-(furan-2-carbonyl)-N'-(3-phenylpropyl)guanidine;
N-(4-methylbenzoyl)-N'-(2-benzylthioethyl)guanidine;
N-(4-methylbenzoyl)-N'-(1-indanyl)guanidine;
N-(N-(4-chlorobenzoyl)-N'-(1-indanyl)guanidine;
N-(3,4-dichlorobenzoyl)-N'-(1-indanyl)guanidine;
N-(1-naphthoyl)-N'-[(imidazol-1-yl)-3-propyl]guanidine;
N-(furan-2-carbonyl)-N'-[(imidazol-1-yl)-3-propyl]guanidine;
N-(4-chlorobenzoyl)-N'-(2-benzylthioethyl)guanidine;
N-(3,4-dichlorobenzoyl)-N'-(2-benzylthioethyl)guanidine;
N-(1-naphthoyl)-N'-(2-benzylthioethyl)guanidine;
N-(thiophen-2-carbonyl)-N'-(2-benzylthioethyl)guanidine;
N-(4-methylbenzoyl)-N'-[(thiophen-2-yl)-2-ethyl]guanidine;
N-(3,4-dichlorobenzoyl)-N'-[(thiophen-2-yl)-2-ethyl]guanidine;
N-(3,4,5-trimethoxybenzoyl)-N'-[(thiophen-2-yl)-2-ethyl]guanidine;
N-(furan-2-carbonyl)-N'-[(thiophen-2-yl)-2-ethyl]guanidine;
N-(thiophen-2-carbonyl)-N'-[(thiophen-2-yl)-2-ethyl]guanidine;
N-(2,3-dichlorobenzoyl)-N'-(4-phenylbutyl]guanidine;
N-(2,5-dichlorobenzoyl)-N'-(4-phenylbutyl]guanidine;
N-(2,6-dichlorobenzoyl)-N'-(4-phenylbutyl]guanidine;
N-(2,6-dichlorophenylacetyl)-N'-benzylguanidine;
N-(4-methylbenzoyl)-N'-(2-phenoxyethyl)guanidine;
N-(benzoyl)-N'-[indol-3-yl-2-yl]guanidine;
N-(1-naphthoyl)-N'-(4-chlorobenzyl)guanidine; and N-(3,4-dichlorobenzoyl)-N'-[(imidazol-1-yl)-3-propyl]guanidine;

and pharmaceutically acceptable salts thereof.

Compounds of the invention can be suitably prepared by one or more of several routes which are generally depicted in the following Scheme.

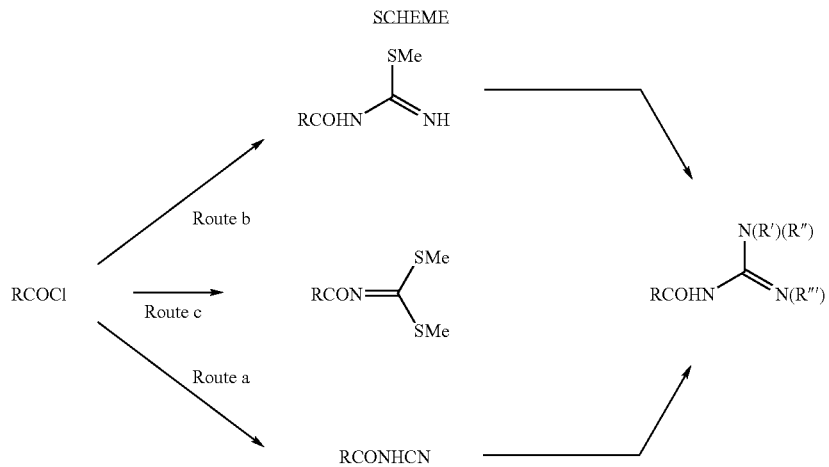

SCHEME

More specifically, as generally depicted in "Route a" above, compounds of the invention can be prepared by reaction of a suitable amine precursor compound with a suitable substituted cyanamide compound that provides the desired R group of compounds of Formulae I through X as well as Formulae I' through X'.

Suitable amine precursor compounds include e.g. a substituted or unsubstituted aromatic amine, a substituted or unsubstited arylalkylamine, a substituted or unsubstituted indolinyl (or derivative thereof compound to prepare compounds of Formula II or II', substituted or unsubstituted 1,2,3,4-tetrahydroquinolinyl (or derivative thereof) compound to prepare compounds of Formula III or III', or an optionally substituted benz[cd]indolinyl compound, optionally substituted 5,6-dihydrophenanthridinyl compound, optionally substituted 2,3,4,5-tetrahydro-[1,5]-benzothiazepine compounds (or derivative thereof, e.g. where Y is other atom), 2a,3,4,5-tetrabenz[cd]indoline compound, 5,6,11,12-tetrahydrodiben[b,f]azocine compound, etc. to prepare compounds of Formulae III through X as well as Formulae III' through X'. A secondary amine can be employed to prepare compounds of Formulae I and I' where $R^2$ is other than hydrogen. For example, an N-methylaniline or other N-alkylaniline can be employed to provide an alkyl $R^2$ substituent for compounds of Formulae I and I'.

Suitable cyanamide compounds will include aryloylcyanamide compounds (i.e. aryl(C=O)NHCN) such as substituted or unsubstituted benzoylcyanamide and the like; an arylalkanoyl cyanamide such as substituted or unsubstituted phenylacetylcyanamide ($C_6H_5COCH_2NHCN$) and the like; a cyclic alkanoyl cyanamide such as admantancarbonylcyanamide and the like; or a heteroaromatic (carbonyl) cyanamide or a heteroalicyclic(carbonyl) cyanamide such as (2-thiophenecarbonyl)cyanamide, (3-thiophenecarbonyl)cyanamide, (1-furanylcarbonyl)cyanamide, (2-furanylcarbonyl)cyanamide, (1-pyridylcarbonyl)cyanamide, (2-pyridylcarbonyl)cyanamide, (3-pyridylcarbonyl)cyanamide, (1-tetrahydrofuranylcarbonyl)cyanamide, (2-tetrahydrofuranylcarbonyl)cyanamide and the like; or (for compounds of Formulae I' through X') an aralkyl, heteroaryl alkyl or heteroalicyclic alkyl reagant such as e.g. methyl phenylacetate and the like. See the examples which follow.

The cyanamide reactants can be readily prepared, e.g. by reaction of the corresponding substituted carbonylchloride reactant with cyanamide under suitable conditions, e.g. in the presence of base with stirring at room temperature until reaction completion. The reaction solution with the thus formed substituted cyanamide then can be neutralized and the product isolated by standard procedures. See the Examples which follow for exemplary conditions.

Typically a salt (e.g. an HCl salt) of the amine precursor compound is reacted with the substituted cyanamide reagent. The amine precursor can be reacted with the substituted cyanamide reagent in a suitable solvent such as chlorobenzene, toluene or xylene with heating (e.g. reflux temperature) until reaction completion, e.g. 2 or more hours.

As generally depicted in "Route b" above, compounds of the invention also can be prepared by reaction of a substituted carbonylisothiourea (RCONHC(=NH)SCH$_3$ in above Route b) and a substituted amine precursor compound, typically a substituted aliphatic amine such as a arylalkylamine, e.g. $NH_2CH_2CH_2CH_2CH_2C_6H_5$. This "Route b" is particularly suitable for synthesis of compounds of Formulae I or II where the substituent X is alkylene.

The isothiourea reagent can be readily prepared by reaction of S-methylisothiourea with a desired substituted carbonyl chloride such as a benzoyl chloride compound in the presence of base and in a suitable solvent such as aqueous diethyl ether at room temperature with stirring overnight. For exemplary conditions, see Example 5, Part I; Example 6, Part I; Example 7, Part I; and Example 8, Part I, which follow. The thus formed isothiourea derivative is then reacted with the substituted amine in the presence of base such as triethylamine in a suitable solvent such as toluene, chlorobenzene or other aromatic solvent with heating, e.g. reflux temperature. See Example 5, Part I; Example 6, Part I; Example 7, Part I; and Example 8, Part I, which follow for exemplary conditions.

As generally depicted in "Route c" above, compounds of the invention that contain an N"-substituent that is other than hydrogen (i.e. one or both of $R^1$ in Formulae I through X or Formulae I' through X' is other than hydrogen) can be suitably prepared by reaction of a substituted carbimidodithiolate (RCON═C(SCH$_3$)$_2$ in above Route c) and sequential reactions of substituted amine precursor compounds. The substituted carbimidodithiolate can be prepared by reaction of a desired substituted amide compound with carbon disulfide in a suitable solvent such as tetrahydrofuran and in the presence of base such as sodium hydride. The isolated substituted carbimidodithiolate compound is reacted with a slight molar excess of a desired substituted amine (provides the desired R group). The resultant thiourea is further reacted with a substituted amine to provide N″ substitution. See Example 9 which follows for exemplary conditions.

As discussed above, the present invention includes methods for treating preventing certain neurological disorders, including the consequences of stroke, heart attack and traumatic head or brain injury, epilepsy or neurodegenerative diseases comprising the administration of an effective amount of one or more compounds of the invention to a subject including a mammal, such as a primate, especially a human, in need of such treatment. In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include e.g. heart attack, stroke and/or persons suffering from cardiac arrest neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure involving extra-corporal circulation such as e.g. a bypass procedure. Subjects suffering from or susceptible to peripheral necropathy can be treated in accordance with the invention by administration of an effective amount of one or more compounds of Formulae I through X or Formulae I' through X'.

The invention in particular provides methods for treatment which comprise administration of one or more compounds of the invention to a patient that is undergoing surgery or other procedure where brain or spinal cord ischemia is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurism or hemorrhage. Thus, an effective amount of one or more compounds of the present invention could be administered pre-operatively or peri-operatively to reduce such risks associated with carotid endarterectomy, or other post-surgical neuorological deficits.

The invention further includes methods for prophylaxis against neurological deficits resulting from e.g. coronary artery bypass graft surgery and aortic valve replacement surgery, or other procedure involving extra-corporal circulation. Those methods will comprise administering to a patient undergoing such surgical procedures an effective amount of one or more compounds of the invention, typically either pre-operatively or peri-operatively.

The invention also provides methods for prophylaxis and treatment against neurological injury for patients undergoing myocardial infarction, a procedure that can result in ischemic insult to the patient. Such methods will comprise administering to a patient undergoing such surgical procedure an effective amount of one or more compounds of the invention, typically either pre-operatively or peri-operatively.

Also provided are methods for treating or preventing neuropathic pain such as may experienced by cancer patients, persons having diabetes, amputees and other persons who may experience neuropathic pain. These methods for treatment comprise administration of an effective amount of one or more compounds of the invention to a patient in need of such treatment.

The invention also provides methods for treatment and prophylaxis against retinal ischemia or degeneration and resulting visual loss. For example, a compound of the invention can be administered parenterally or by other procedure as described herein to a subject a suffering from or susceptible to ischemic insult that may adversely affect retinal function, e.g., significantly elevated intraocular pressures, diseases such as retinal artery or vein occlusion, diabetes or other ischemic ocular-related diseases. Post-ischemic administration also may limit retinal damage. The invention also includes methods for treating and prophylaxis against decreased blood flow or nutrient supply to retinal tissue or optic nerve, or treatment or prophylaxis against retinal trauma or optic nerve injury. Subjects for treatment according to such therapeutic methods of the invention may be suffering or susceptible to retinal ischemia that is associated with atherosclerosis, venous capillary insufficiency, obstructive arterial or venous retinopathies, senile macular degeneration, cystoid macular edema or glaucoma, or the retinal ischemia may be associated with a tumor or injury to the mammal. Intravitreal injection of a compound of the invention also may be a preferred administration route to provide more direct treatment to the ischemic retina.

The invention also provides methods for treatment of a subject suffering from shingles as well as treatment of a person suffering from or susceptible to migraines, particularly to alleviate the pain and discomfort associated with those disorders. As discussed above, compounds of the invention are also useful to treat persons suffering from various types of pain, including chromic pain. These methods comprise administration of an effective amount of one or more compounds of the invention to a patient in need of treatment.

The invention further provides a method of treating Korsakoff's disease, a chronic alcoholism-induced condition, comprising administering to a subject including a mammal, particularly a human, one or more compounds of the invention in an amount effective to treat the disease. Compounds of the invention are anticipated to have utility for the attenuation of cell loss, hemorrhages and/or amino acid changes associated with Korsakoff's disease.

As discussed above, the invention also includes methods for treating a person suffering from or susceptible to cerebral palsy, emesis, narcotic withdrawal symptoms and age-dependent dementia, comprising administering to a subject including a mammal, particularly a human, one or more compounds of the invention in an amount effective to treat the condition.

The invention also includes methods for treatment of infections, including Gram-negative and Gram-positive bacterial infections, comprising administering a combination of 1) an aminoglycoside antibiotic, and 2) a compound of Formulae I, IA, IB, II, III, IV, V, VI, VII, VIII, IX and/or X as well as Formulae I', IA', IB', II', III', IV', V', VI', VII', VIII', IX' and/or X' as defined herein. A wide variety of aminoglycoside antibiotics are suitable for use in the formulations of the invention. Typically, suitable aminoglycoside antibiotics contain two or more amino sugars (aminoglycosides) connected to an amino-cyclitol nucleus. Exemplary aminoglycoside antibiotics preferred for use in formulations of the present invention include clinical agents such as gentamycin, amikacin, kanamycin, streptomycin, paromoycin, neomycin, netilmicin and tobramycin. Other suitable aminoglycosides include seldomycins, sisomycins, aurimycin, lividomycins, streptothricins, hybrimycins, coralinomycin, butirosin, strepomutins, nebramycins, tenebrimycins, ribostamycins, destomycins, trehalosamines, myomycins, fortimicins, mutamicins and kasugamycin. Suitable aminoglycoside antibiotics are also disclosed in U.S. Pat. Nos. 5,508,269; 4,645,760; and 4,380,625. It should be appreciated however that the present invention is not limited by any particular aminoglycoside antibiotic, and the invention is applicable to any aminoglycoside antibiotic now known or subsequently discovered or developed. The aminoglycoside and one or more compounds of the invention may be administered simultaneously, in the same or different pharmaceutical formulations, or sequentially. Preferably, the components of the combination are administered substantially simultaneously, e.g. in a unitary pharmaceutical composition containing the two components. Preferred methods and compositions that comprise an aminoglycoside in combination with a compound of the invention will be effective against infections previously treated with aminoglycoside antibiotics, but with the significant advantage of decreased occurrence of ototoxicity relative to use of an aminoglycoside antibiotic alone.

As discussed above, preferred compounds of the invention in a standard anticonvulsant in vivo audiogenic test, such as the audiogenic mouse assay of Example 11 which follows, where DBA/2 mice about 20–23 days old are injected intraperitoneally with a test compound 30 minutes prior to being placed in a bell jar with exposure to auditory stimulus of 12 KHz sine wave at 110–120 db. References herein in vivo "audiogenic assay" are intended to refer to that protocol. Generally preferred compounds exhibit 20% or more inhibition (relative to subjects treated with vehicle control only) at a dose of 20 mg/kg, more preferably about 50% or more inhibition at a dose of 20 mg/kg in such an in vivo audiogenic assay. As discussed above, activity in the audiogenic assay has been recognized as indicative that a test compound has neuroprotective properties. See, e.g., M. Tricklebank et al., *European Journal of Pharmacology*, supra; T. Seyfried, *Federation Proceedings*, supra.

The invention also provides methods for determining binding activity of compounds of the invention as well as in vitro and in vivo binding activity diagnostic methods using one or more radiolabelled compounds of the invention, e.g., a compound of the invention that is labeled with $^{125}$I, tritium, $^{32}$P, $^{99}$Tc, or the like, preferably $^{125}$I. For instance, a compound of the invention having a phenyl or other aryl substituent that is ring substituted with one or more $^{125}$I groups can be administered to a mammal and the subject then scanned for binding of the compound. Specifically, single photon emission computed tomography ("SPECT") can be employed to detect such binding. Such an analysis of the mammal could e.g. aid in the diagnosis and treatment of acute cerebral ischemia. That is, a labeled compound of the invention will selectively bind to ischemic tissue of e.g. a subject's brain to differentiate between ischemic and non-ischemic tissue and thereby assess trauma or other injury to the brain.

Accordingly, the invention includes compounds of the invention that contain a radiolabel such as $^{125}$I, tritium, $^{32}$P, $^{99}$Tc, or the like, preferably $^{125}$I. Such radiolabelled compounds can be suitably prepared by procedures known in the synthesis art. For example, a compound of the invention having an aromatic group, such as phenyl, that has a bromo or chloro ring substituent can be employed in an exchange labeling reaction to provide the corresponding compound having an $^{125}$I ring substituent.

Compounds of the invention may be used in therapy in conjunction with other medicaments. For example, for treatment of a stroke victim or a person susceptible to stroke, one or more compounds of Formula I may be suitably administered together with a pharmaceutical targeted for interaction in the blood clotting mechanism such as streptokinase, tPA, urokinase and other agents that lyse clots. Also, one or more compounds of the invention may be administered together with agents such as heparin and related heparin-based compounds, acenocoumarol or other known anticoagulants.

The compounds of this invention can be administered intranasally, orally or by injection, e.g., intramuscular, intraperitoneal, subcutaneous or intravenous injection, or by transdermal, intraocular or enteral means. The optimal dose can be determined by conventional means. Compounds of the invention are suitably administered to a subject in the protonated and water-soluble form, e.g., as a pharmaceutically acceptable salt of an organic or inorganic acid, e.g., hydrochloride, sulfate, hemi-sulfate, phosphate, nitrate, acetate, oxalate, citrate, maleate, mesylate, etc.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, enteral or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

For topical applications, formulations may be prepared in a topical ointment or cream containing one or more compounds of the invention. When formulated as an ointment, one or more compounds of the invention suitably may be employed with either a paraffinic or a water-miscible base. The one or more compounds also may be formulated with an oil-in-water cream base. Other suitable topical formulations include e.g. lozenges and dermal patches.

Intravenous or parenteral administration, e.g., sub-cutaneous, intraperitoneal or intramuscular administration are preferred. The compounds of this invention are particularly valuable in the treatment of mammalian subjects, e.g., humans, to provide neuroprotective therapy and/or prophylaxis. Typically, such subjects include those afflicted with neurodegenerative diseases such as Parkinson's disease, Huntington's disease, Amyotrophic Lateral Sclerosis, Alzheimer's disease, Down's Syndrome and Korsakoff's disease. Also suitable for treatment are those subjects suffering from or likely to suffer from nervous system dysfunctions resulting from, for example, epilepsy or nerve cell degeneration which is the result of hypoxia, hypoglycemia, brain or spinal chord ischemia or brain or spinal chord trauma. As discussed above, typical candidates for treatment include heart attack, stroke, brain or spinal cord injury patients, patients undergoing major surgery where brain or spinal cord ischemia is a potential complication and patients such as divers suffering from decompression sickness due to gas emboli in the blood stream.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of the invention, particularly when using the more potent compound(s) of the invention, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule. Such sub-doses may be administered as unit dosage forms, e.g., containing from 0.05 to 10 milligrams of compound(s) of the invention, per unit dosage, preferably from 0.2 to 2 milligrams per unit dosage.

Compounds of the invention also should be useful as rubber accelerators. See U.S. Pat. No. 1,411,713 for a discussion of rubber accelerator applications.

The entire text of all documents cited herein are incorporated by reference herein. The following non-limiting examples are illustrative of the invention.

GENERAL COMMENTS

Melting points were determined in open capillary tubes on a Mel-Temp II apparatus and are uncorrected. Yields are of isolated products and were not optimized. $^1$H-NMR were run on a Varian Gemini 300 MHz spectrophotometer and the chemical shifts were reported in ppm ($\delta$) relative to the residual signal of deutrated solvent (CHD$_2$OD 3.30, CDCl$_3$ 7.26). HPLC purity determinations were carried out using a Beckman 126 gradient system with UV detection at 220 nm. Linear 30 minutes gradient: 2 to 98% CH$_3$CN in H$_2$O (0.1% TFA) Column: Ultrasphere ODS (AC-2) 5 mm 4.6×250 mm with C-18 guard column, flow rate 1 ml/min.

EXAMPLE 1

Synthesis of N-(4-methylbenzoyl)-N'-(4-isopropylphenyl)guanidine, hydrochloride (Formula I: hydrochloride salt of R=4-CH$_3$C$_6$H$_4$; each R$^1$=R$^2$=H; X=chemical bond; R$^3$=4-isopropylphenyl)

Part I: 4-methylbenzoylcyanamide

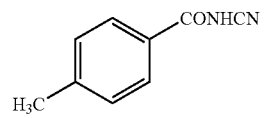

To a solution of cyanamide (1.05 g, 0.025 mmol) in 25 ml of sodium hydroxide (10%) was added slowly to a solution of 4-methylbenzoyl chloride (3.3 ml, 0.025 mmol) in ether (8 ml). The reaction mixture was stirred at room temperature for 1 hour. The reaction mixture then was cooled in ice bath and acidified with hydrochloric acid (10%) to pH 2. The white solid separated was filtered, washed with water, later hexanes and dried under high vacuum to give the N-(4-methylbenzoyl)cyanamide (3.4 g); m.p. 140–142° C. (lit m.p. 149–150° C.); purity 88% HPLC; $^1$H-NMR (CD$_3$OD) $\delta$ 2.42 (s, 3H, CH$_3$), 7.38 (d, 2H, ArH), 7.78 (d, 2H, ArH).

Part II: N-(4-methylbenzoyl)-N'-(4-isopropylphenyl) guanidine, hydrochloride

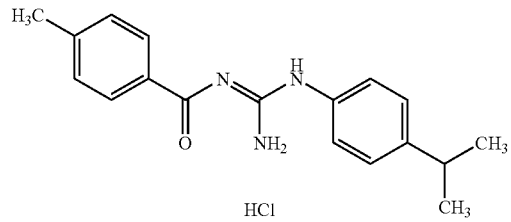

A mixture of N-(4-methylbenzoylcyanamide) (160 mg, 1 mmol) and 4-isopropylaniline•hydrochloride (185 mg [prepared from 4-isopropylaniline and hydrogen chloride (1M in ether)]) in toluene (4 ml) was refluxed for 3 hours. The reaction mixture was cooled to room temperature, the precipitated white solid was filtered, washed with toluene and finally with hexanes to afford the title product, (268 mg, 78%); m.p. 208–210° C.; purity 99.3% (HPLC); $^1$H-NMR (CD$_3$OD) $\delta$ 1.28 (2s, 6H, CH$_3$), 2.42 (s, 3H, Ar—CH$_3$), 3.02 (m, 1H, CH), 7.38 (d, 2H, ArH), 7.42 (m, 4H, ArH), 8.0 (d, 2H, ArH).

EXAMPLE 2

Preparation of N-(1-adamantancarbonyl)-1-indolinylcarboxamidine, hydrochloride ((Formula II: hydrochloride salt of R=1-adamantyl; each $R^1=R^2=R^3=H$)

Part I: Adamantancarbonylcyanamide

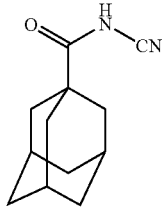

To a solution of cyanamide (2.52 g, 0.06 mol) in 24 ml of sodium hydroxide (10%) was added slowly to a solution of 1-adamantanecarbonylchloride (4 g, 0.02 mol) in ether (15 ml). The reaction mixture was stirred at room temperature overnight. The reaction mixture was extracted with ether and the aqueous layer was cooled in ice bath and acidified with hydrochloric acid (10%) to pH 2. The precipitated white solid was filtered, washed with water, later hexanes and dried under high vacuum to give the N-(1-adamantancarbonyl)cyanamide (3.2 g, 78%); m.p. 164–166° C. (lit m.p. 168–170° C.); purity 94% HPLC; $^1$H-NMR (CD$_3$OD) δ 1.45–2.16 (m, 15H, CH$_2$ and CH).

Part II: N-(1-adamantancarbonyl)-1-indolinylcarboxamidine, hydrochloride

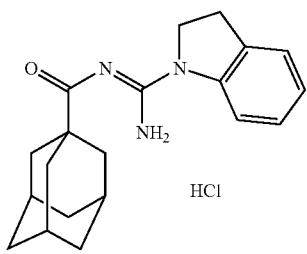

A mixture of N-(1-adamantanecarbonyl)cyanamide (200 mg, 0.88 mmol) and indoline hydrochloride (155 mg [prepared from indoline and hydrogen chloride (1M in ether)]) in toluene (4 ml) was refluxed for 3 hours. The reaction mixture was cooled to room temperature, the precipitated white solid was filtered, washed with toluene and finally with hexanes to afford the title product, (339 mg, 78%); m.p. 252–256° C.; Purity 99% (HPLC); $^1$H-NMR (CD$_3$OD) δ 1.65 (m, 15H, CH$_2$ and CH), 3.2 (t, 2H, ArCH$_2$), 4.2 (t, 2H, NCH$_2$), 7.25 (m, 1H, arH), 7.36 (m, 2H, ArH), 7.42 (m, 1H, ArH).

EXAMPLE 3

Preparation of N-(phenylacetyl)-N'-(4-t-butylphenyl)guanidine, hydrochloride (Formula I: hydrochloride salt of $R=C_6H_5$; each $R^1=R^2=H$; X=chemical bond; $R^3$=4-tert-butylphenyl)

Part I: Phenylacetylcyanamide

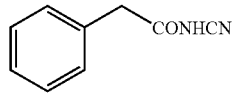

This compound was prepared in 83% yield by the method described in Example 2, Part I above using phenylacetyl chloride in place of adamantane-1-carbonyl chloride. Phenylacetylcyanamide: a white solid; purity 92% (HPLC); $^1$H-NMR (CD$_3$OD) δ 2.3 (s, 2H), 7.25–7.45 (m, 5H).

Part II: N-(Phenylacetyl)-N'-(4-t-butylphenyl)guanidine, hydrochloride

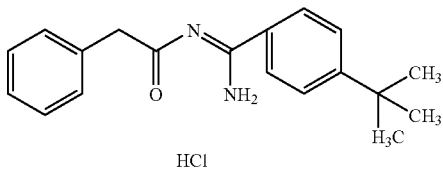

Synthesis of this compound was achieved by the method set forth in Example 1, Part II above with the use of phenylacetylcyanamide in place of 4-methylbenzoylcyanamide and using 4-t-butylaniline hydrochloride instead of 4-isopropylaniline hydrochloride respectively. Yield 69%; m.p. 182–186° C.; Purity 86% (HPLC); $^1$H-NMR (CD$_3$OD) δ 1.38 (s, 9H, CH$_3$), 3.84 (s, 2H, CH$_2$), 7.3 (d, 2H, ArH), 7.3–7.45 (m, 5H, ArH), 7.6 (d, 2H, ArH).

EXAMPLE 4

Preparation of N-(2-thiophenecarbonyl)-N'-(4-benzyloxyphenyl)guanidine, hydrochloride (Formula I: hydrochloride salt of R=2-thiophenyl; each $R^1=R^2=H$; X=chemical bond; $R^3$=4-$C_6H_5CH_2OC_6H_4$-)

Part I: (2-Thiophenecarbonyl)cyanamide

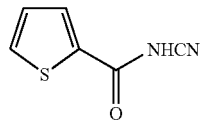

This compound was prepared in 73% yield by the method described in Example 2, Part I above using 2-thiophenecarbonylchloride in place of adamantane-1-carbonyl chloride. N-(2-thiophenecarbonyl)cyanamide: a white solid; purity 96% (HPLC); $^1$H-NMR (CD$_3$OD) δ 7.2 (m, 1H), 7.8 (d, 1H), 7.9 (d, 1H).

Part II: N-(2-Thiophenecarbonyl)-N'-(4-benzyloxyphenyl)guanidine, hydrochloride

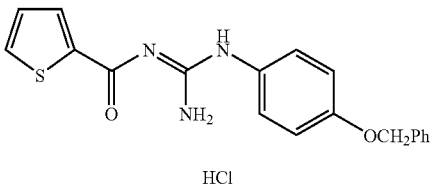

HCl

Synthesis of this compound was achieved by the method set forth in Example 1, Part II above with the use of N-(2-thiophenecarbonyl)cyanamide in place of N-(4-methylbenzoylcyanamide) and using 4-benzylcyanamide and using 4-benzyloxyaniline hydrochloride instead of 4-isopropylaniline hydrochloride respectively. Yield 61%; m.p. 198–202° C.; Purity 93% (HPLC); $^1$H-NMR (CD$_3$OD) δ 5.18 (s, 2H, CH$_2$), 7.18 (d, 2H), 7.22–7.4 (m, 6H), 7.44 (d, 2H), 7.9 (d, 1H), 8.18 (d, 1H).

EXAMPLE 5

Preparation of N-(4-methylbenzoyl)-N'-(4-phenylbutyl)guanidine, hydrochloride (Formula I: hydrochloride salt of R=4-CH$_3$C$_6$H$_4$; each R$^1$=R$^2$=H; X=CH$_2$CH$_2$CH$_2$CH$_2$; R$^3$=C$_6$H$_5$)

Part I: N-(4-Methylbenzoyl)-S-methylisothiourea

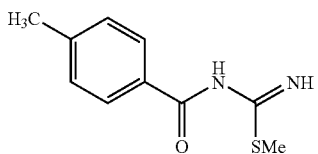

A solution of 2-methyl-2-thiopseudourea sulfate (6.9 g, 0.025 mol) in 30 ml of sodium hydroxide (4%) was added a solution of 4-methylbenzoyl chloride (3.4 g, 0.022 mol) in ether (10 ml) at room temperature. The reaction mixture was stirred overnight and the precipitated solid was filtered, washed with water, later hexanes and dried under high vacuum. N-(4-methylbenzoyl)-S-methylisothiourea: yield 4.60 g (quantitative); purity 98% (HPLC); $^1$H-NMR (CD$_3$OD) δ 2.4 (s, 3H, CH$_3$), 2.6 (s, 3H, SMe), 7.2 (d, 2H, ArH), 8.1 (d, 2H, ArH).

Part II: N-(4-methylbenzoyl)-N'-(4-phenylbutyl) guanidine, hydrochloride

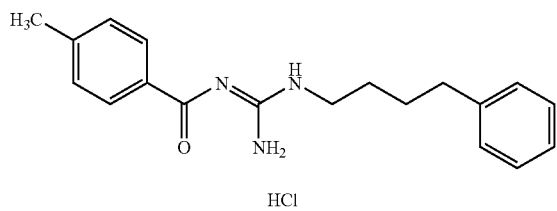

HCl

Phenylbutyl amine (0.75 ml, 4.75 mmol) and triethylamine (0.7 ml, 5 mmol) was added to a suspension of the thiourea derivative (1.04 g, 5 mmol), prepared in Part I, in touene (10 ml). The reaction mixture was heated in an oilbath to reflux and maintained at reflux for 3 hours. The free base separated on cooling was filtered, washed with hexanes and dried to afford the solid (1.3 g).

The free base (1.3 g) was dissolved in methanol (30 ml) and dichloromethane (25 ml) and cooled in an ice water bath. Hydrogen chloride (1M in ether, 20 ml) was added, stirred for 30 minutes, concentrated under reduced pressure. N-(4-methylbenzoyl)-N'-(4-phenylbutyl)guanidine, hydrochloride: white solid (1.43 g, 84%); m.p. 166–170° C.; Purity: 99% (HPLC); $^1$H-NMR (CD$_3$OD) δ 1.74 (m, 4H, CH$_2$), 2.43 (s, 3H, CH$_3$), 2.69 (t, 2H, CH$_2$), 3.38 (t, 2H, CH$_2$), 7.2 (m, 5H, ArH), 7.4 (d, 2H, ArH), 7.9 (d, 2H, ArH).

EXAMPLE 6

Preparation of N-(4-methoxybenzoyl)-N'-(4-phenylbutyl)guanidine, hydrochloride (Formula I: hydrochloride salt of R=4-CH$_3$OC$_6$H$_4$; each R$^1$=R$^2$=H; X=CH$_2$CH$_2$CH$_2$CH$_2$; R$^3$=C$_6$H$_5$)

Part I: N-(4-Methoxybenzoyl)-S-methylisothiourea

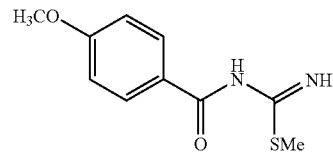

Synthesis of this compound was achieved by the method set forth in Example 5, Part I above with the use of 4-methoxybenzoyl chloride in place of 4-methylbenzoyl chloride. N-(4-methoxybenzoyl)-S-methylisothiourea: white solid (83% yield); Purity 99% (HPLC); $^1$H-NMR (CD$_3$OD) δ 2.57 (s, 3H, SCH$_3$), 3.86 (s, 3H, OCH$_3$), 6.94 (d, 2H, ArH), 8.15 (d, 2H, ArH).

Part II: N-(4-Methoxybenzoyl)-N'-(4-phenylbutyl) guanidine, hydrochloride

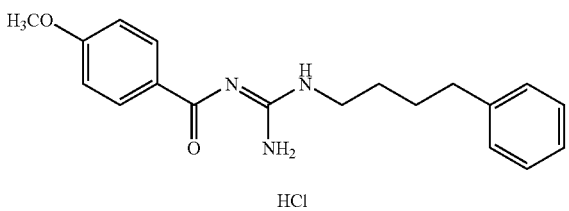

HCl

Preparation of this compound was carried out by the method as described in Example 5, Part II above using 4-methoxybenzoyl-S-methylisothiourea in place of 4-methylbenzoyl-S-methylisothiourea. N-(4-methoxybenzoyl)-N'-(4-phenylbutyl)guanidine, hydrochloride: white solid (55%); m.p. 172–174° C.; Purity 99% (HPLC); $^1$H-NMR (CD$_3$OD) δ 1.74 (m, 4H, CH$_2$), 2.67 (t, 2H, CH$_2$), 3.37 (t, 2H, CH$_2$), 3.89 (s, 3H, OCH$_3$), 7.10 (d, 2H, ArH), 7.22 (m, 5H, ArH), 7.97 (d, 2H, ArH).

EXAMPLE 7

N-(2-thiophenecarbonyl)-N'-(2-phenylethyl)guanidine, hydrochloride (Formula I: hydrochloride salt of R=2-thiophenyl; each $R^1=R^2=H$; $X=CH_2CH_2$; $R^3=C_6H_5$)

Part I:
N-(2-Thiophenecarbonyl)-S-methylisothiourea

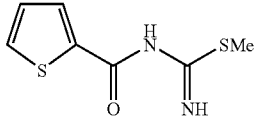

Synthesis of this compound was achieved by the method set forth in Example 5, Part I above with the use of 2-thiophenecarbonyl chloride in place of 4-methylbenzoyl chloride. N-(2-thiophenecarbonyl)-S-methylisothiourea: white solid (73% yield); Purity 91.2% (HPLC); $^1$H-NMR (CD$_3$OD) δ 2.76 (s, 3H, SCH$_3$), 7.26 (m, 1H, ArH), 8.01 (d, 1H, ArH), 8.12 (d, 1H, ArH).

Part II: N-(2-Thiophenecarbonyl)-N'-(2-phenylethyl)guanidine, hydrochloride

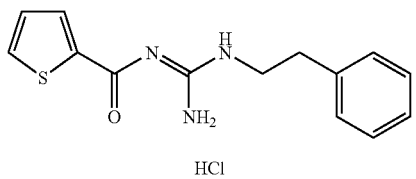

Preparation of this compound was carried out by the method as described in Example 5, Part II above using N-(2-thiophenecarbonyl)-S-methylisothiourea in place of 4-methylbenzoyl-S-methylisothiourea and 2-phenylethylamine instead of 4-phenylbutylamine respectively. N-(2-thiophenecarbonyl)-N'-(2-phenylethyl)guanidine, hydrochloride: white solid (58%); m.p. 198–200° C.; Purity 97% (HPLC); $^1$H-NMR (CD$_3$OD) δ 3.00 (t, 2H, CH$_2$), 3.65 (t, 2H, CH$_2$), 7.2 (d, 1H, ArH), 7.28 (m, 5H, ArH), 7.97 (d, 2H, ArH).

EXAMPLE 8

N-(4-Butoxybenzoyl)-N'-[2-(indol-3-yl)ethyl]guanidine, hydrochloride (Formula I: hydrochloride salt of R=4-CH$_3$(CH$_2$)$_3$OC$_6$H$_4$; each $R^1=R^2=H$; $X=CH_2CH_2$; $R^3$=3-indolyl)

Part I: N-(4-Butoxybenzoyl)-S-methylisothiourea

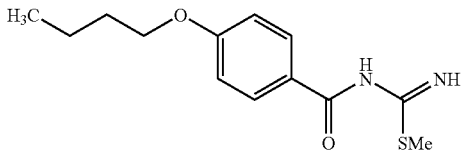

This compound was prepared following the method as described in Example 6, Part I above using 4-butoxybenzoyl chloride in place of 4-methoxybenzoyl chloride. N-(4-butoxybenzoyl)-S-methylisothiourea: white solid (85%); Purity 95% (HPLC); $^1$H-NMR (CD$_3$OD) δ 1.0 (t, 3H, CH$_3$), 1.50 (m, 2H, CH$_2$), 1.78 (m, 2H, CH$_2$), 2.56 (s, 3H, SCH$_3$), 4.03 (t, 2H, OCH$_2$), 6.93 (d, 2H, ArH), 8.14 (d, 2H, ArH).

Part II: N-(4-Butoxybenzoyl)-N'-[2-(indol-3-yl)ethyl]guanidine, hydrochloride

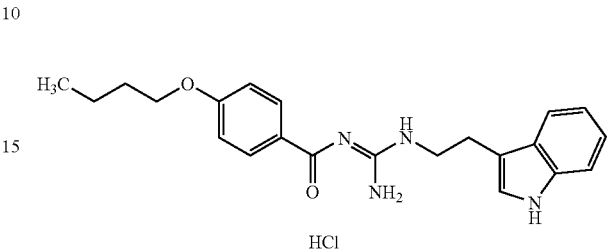

Preparation of this compound was carried out by the method as described in Example 5, Part II above using N-(4-butoxybenzoyl)-S-methylisothiourea in place of 4-methylbenzoyl-S-methylisothiourea and 3-(2-aminoethyl)indole (tryptamine) instead of 4-phenylbutylamine respectively. N-(4-butoxybenzoyl)-N'-[2-(indol-3-yl)ethyl]guanidine, hydrochloride: solid (yield 28%); m.p. 158–162° C.; Purity 95% (HPLC); $^1$H-NMR (CD$_3$OD) δ 0.99 (t, 3H, CH$_3$), 1.49 (m, 2H, CH$_2$), 1.76 (m, 2H, CH$_2$), 3.28 (t, 2H, CH$_2$), 3.69 (t, 2H, CH$_2$), 4.05 (t, 2H, CH$_2$), 7.04 (m, 4H, ArH), 7.2 (d, 1H), 7.32 (d, 1H, ArH), 7.56 (d, 1H, ArH), 7.86 (d, 2H, ArH).

EXAMPLE 9

N-(4-Methylbenzoyl)-N'-(4-phenylbutyl)-N''-methylguanidine, hydrochloride (Formula I: hydrochloride salt of R=4-CH$_3$C$_6$H$_4$; first $R^1$=CH$_3$; second $R^1$=H; $R^2$=H; $X=CH_2CH_2CH_2CH_2$; $R^3=C_6H_5$)

Part I: Dimethyl N-(4-methylbenzoylcarbimidodithiolate)

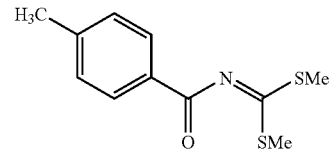

A mixture of 4-methylbenzamide (1.35 g, 0.01 mol) in anhydrous tetrahydrofuran (50 ml), carbon disulfide (3 g, 0.039 mol), and methyl iodide (4.5 g, 0.032 mol), and sodium hydride (0.85 g, 60% dispersion in oil, 0.02 mol) was stirred at room temperature overnight. The reaction mixture was poured onto ice, extracted with ethyl acetate (3×30 ml), washed with water, dried and concentrated to give an oil. This solidified on standing and was crystallized from hexanes as bright yellow crystals (0.8 g); m.p. 57–59° C. (lit 60–61° C.); $^1$H-NMR (CDCl$_3$) δ 2.40 (s, 3H, Ar-Me), 2.57 (s, 6H, SMe), 7.25 (d, 2H, ArH), 7.98 (d, 2H, ArH).

Part II: N-(4-methylbenzoyl)-N'-(4-phenylbutyl)-S-Methylthiourea

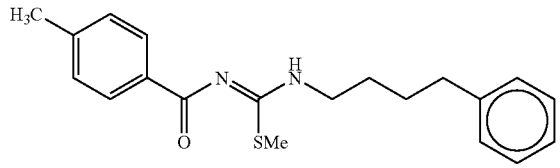

A mixture of dimethyldithiolate (240 mg, mmol, prepared as in Part I) and phenybutylamine (150 mg, mmol) in ethanol (5 ml) was stirred overnight at room temperature. The reaction mixture was concentrated and the oil obtained was repeatedly coevaporated with dichloromethane, upon which solid separated. This solid was triturated with hexanes, filtered and dried. N-(4-methylbenzoyl)-N'-(4-phenylbutyl)-S-Methylthiourea: white solid (80 mg); $^1$H-NMR (CDCl$_3$) δ 1.85 (m, 4H, CH$_2$), 2.38 (s, 3H, ArMe), 2.61 (s and t, 5H, CH$_2$ and Sme), 3.35 (t, 2H, CH$_2$), 7.2 (m, 5H, ArH), 7.28 (d, 2H, ArH), 8.12 (d, 2H, ArH).

Part III: N-(4-Methylbenzoyl)-N'-(4-phenylbutyl)-N"-methylguanidine, hydrochloride

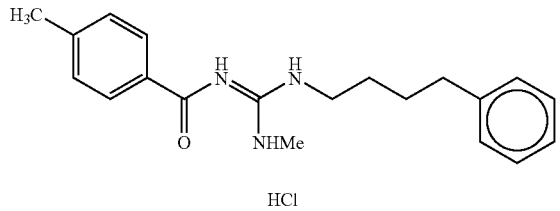

A solution of N-(4-methylbenzoyl)-N'-(4-phenylbutyl)-S-Methylthiourea (80 mg, prepared as in Part II) in 5 ml of methylamine (2M in methanol) was stirred at room temperature for 48 hours. After removal of the solvent the residue was dissolved in methanol (3 ml), and a ethereal solution of hydrogen chloride (5 ml) was added. The solid separated was filtered, washed with ether and dried. Pale yellow solid (50 mg); Purity: 93% (HPLC); $^1$H-NMR (CD$_3$OD) δ 1.71 (m, 4H, CH$_2$), 2.40 (s, 3H, ArCH$_3$), 2.65 (t, 2H, CH$_2$), 3.05 (s, 3H, NMe), 3.4 (t, 2H, CH$_2$), 7.13 (m, 5H, Ar), 7.35 (d, 2H, ArH), 7.82 (d, 2H, ArH).

EXAMPLE 10

N-(2,6-Dichlorophenylacetyl)-N'-benzylguanidine hydrochloride (Formula I': hydrochloride salt of R=2,6-di-C$_6$H$_3$; both R$^1$=H; R$^2$=H; X=CH$_2$; R$^3$=C$_6$H$_5$)

Part I: Benzylguanidine hydrochloride

A mixture of benzylamine hydrochloride (4.3 g, 0.03 mol) and cyanamide (1.3 g, 0.031 mol) in xylenes (15 ml) was heated to reflux for 6 hours. After concentration, the reaction mixture was triturated with ether and the solid separated was filtered and crystallized from methanol to provide a colorless solid (2.38 g); purity: 96.8% (HPLC); $^1$H-NMR (CD$_3$OD) δ 4.41 (s, 2H, CH$_2$), 7.32–7.37 (m, 5H, Ar).

Part II: N-(2,6-Dichlorophenylacetyl)-N'-benzylguanidine hydrochloride

To sodium ethoxide [prepared by reacting sodium (60 mg, 2.61 mmol) and anhydrous ethanol (5 ml)] benzylguanidine hydrochloride (580 mg, 3.12 mmol) was added and refluxed in an oilbath for 1 hour. The reaction mixture was cooled to room temperature and insoluble materials filtered. Methyl 2,6-dichlorophenylacetate (285 mg, 1.3 mmol) (CH$_3$(C=O) CH$_2$(2,6,-di-ClC$_6$H$_3$) was added to the filtrate and refluxed for 2 hours. After cooling to room temperature the reaction mixture was concentrated and converted to the hydrochloride salt by the addition of hydrogen chloride (1M in ether) to provide 310 mg of N-(2,6-dichlorophenylacetyl)-N'-benzylguanidine hydrochloride as a white solid, purity 89.3% (HPLC); $^1$H-NMR (CD$_3$OD) δ 4.38 (s, 4H, CH$_2$), 7.32–7.41 (m, 8H, Ar).

EXAMPLE 11

In vivo Anticonvulsant activity in the DBA/2 mouse model (Mouse audiogenic assay)

The in vivo potency of compounds of the invention is exemplified by data summarized in the Table I below and obtained pursuant to the following protocol.

Compounds were tested for their effectiveness in preventing seizures in DBA/2 mice which have a unique sensitivity to auditory stimulation. Exposure to loud high-frequency sounds can trigger seizure activity in these animals. This sensitivity develops from postnatal day 12 and peaks around day 21 and slowly diminishes as the animals mature. The unusual response to auditory stimulation in this strain of mouse is believed to be due to a combination of early myelination (causing an unusually low excitatory threshold) and delayed development of inhibitory mechanisms.

Mice were injected intraperitoneally with the compound specified in Table I below or with vehicle control, 30 minutes prior to being placed in a bell jar and turning on the auditory stimulus (12 KHz sine wave at 110–120 db). Administered doses are specified in Table I as milligram of compound per kilogram bodyweight of mouse. The auditory stimulus was left on for 60 seconds and mice reactions were timed and recorded. Percentage inhibition was determined with reference to vehicle controls. Results are shown in the Table I below. All compounds were tested in HCl salt form.

TABLE I

| | Audiogenic Response | |
|---|---|---|
| Compound Name | Dose (mg/kg) | % Inhib. |
| N-(4-methylbenzoyl)-N'-(4-isopropylphenyl)-guanidine | 20 | 30 |
| N-(4-methylbenzoyl)-N'-(4-phenylbutyl)guanidine | 20 | 75 |
| | 10 | 16 |
| N-(4-methoxybenzoyl)-N'-(4-phenylbutyl)-guanidine | 20 | 42 |
| N-(4-methoxyphenyl)-N'-(4-isopropylphenyl)guanidine | 20 | 56 |
| N-(4-ethoxyphenyl)-N'-(4-phenylbutyl)guanidine | 20 | 60 |
| N-(4-butoxyphenyl)-N'-(4-phenylbutyl)guanidine | 20 | 97 |

This invention has been described in detail with reference to preferred embodiments thereof. However, it will be appreciated that those skilled in the art, upon consideration of this disclosure, may make modifications and improvements within the spirit and scope of the invention.

What is claimed is:

1. A compound that is:

N-(4-methylbenzoyl)-N'-methyl-N'-(3-methylthiophenyl)guanidine;
N-(4-methylbenzoyl)-N'-methyl-N'-(3-iodophenyl)guanidine;
N-(4-methylbenzoyl)-N'-(1-naphthyl)guanidine;
N-(4-methylbenzoyl)-N'-(4-benzyloxyphenyl)guanidine;
N-(4-methylbenzoyl)-N'-(4-tertbutylphenyl)guanidine;
N-(4-methylbenzoyl)-1-indolinylcarboximidamide;
N-(4-methylbenzoyl)-N'-(4-isopropylphenyl)guanidine;
N-(4-methylbenzoyl)-1-[7-(trifluoromethyl)-1,2,3,4-tetrahydroquinoline] carboximidamide;
N-(4-methylbenzoyl)-1-(1,2,3,4-tetrahydroquinoline)carboximidamide;
N-(4-methylbenzoyl)-N'-(2,5-dibromophenyl)guanidine;
N-(4-methylbenzoyl)-N'-(4-isopropoxyphenyl)guanidine;
N-(4-methylbenzoyl)-N'-(3,4,5-trimethoxyphenyl)guanidine;
N-(4-methylbenzoyl)-N'-(2-isopropylphenyl)guanidine;
N-(2,5-dichlorobenzoyl)-N'-methyl-N'-(3-iodophenyl)guanidine;
N-(2,5-dichlorobenzoyl)-N'-methyl-N'-(3-methylthiophenyl)guanidine;
N-(2,5-dichlorobenzoyl)-N'-(1-naphthyl)guanidine;
N-(2,5-chlorobenzoyl)-N'-(4-benzyloxyphenyl)guanidine;
N-(2,5-dichlorobenzoyl)-N'-(4-isopropylphenyl)guanidine;
N-(2,5-dichlorobenzoyl)-N'-(4-tertbutylphenyl)guanidine;
N-(2,5-dichlorobenzoyl)-1-indolinylcarboximidamide;
N-(2,5-dichlorobenzoyl)-N'-methyl-N'-(4-isopropylphenyl)guanidine;
N-(phenylacetyl)-N'-(4-benzyloxyphenyl)guanidine;
N-(phenylacetyl)-N'-(4-isopropylphenyl)guanidine;
N-(phenylacetyl)-N'-(4-tert-butylphenyl)guanidine;
N-(phenylacetyl)-1-indolinylcarboximidamide;
N-(phenylacetyl)-1-(1,2,3,4-tetrahydroquinoline)carboximidamide;
N-(phenylacetyl)-N'-(4-isopropoxyphenyl)guanidine;
N-(phenylacetyl)-N'-(4-isopropylphenyl)-N'-methylguanidine;
N-(adamantan-1-carbonyl)-N'-methyl-N'-(3-iodophenyl)guanidine;
N-(adamantan-1-carbonyl)-N'-(1-naphthyl)guanidine;
N-(adamantan-1-carbonyl)-N'-(4-benzyloxyphenyl)guanidine;
N-(adamantan-1-carbonyl)-N'-(4-isopropylphenyl)guanidine;
N-(adamantan-1-carbonyl)-N'-(4-tert-butylphenyl)guanidine;
N-(adamantan-1-carbonyl)-1-(indolinyl)carboximidamide;
N-(adamantan-1-carbonyl)-1-(1,2,3,4-tetrahydroquinolinyl)carboximidamide;
N-(adamantan-1-carbonyl)-N'-(2,5-dibromophenyl)guanidine;
N-(adamantan-1-carbonyl)-N'-(4-isopropylphenyl)-N'-methyl)guanidine;
N-(4-chlorobenzoyl)-N'-methyl-N'-(3-iodophenyl)guanidine;
N-(4-chlorobenzoyl)-N'-methyl-N'-(3-methylthiophenyl)guanidine;
N-(4-chlorobenzoyl)-N'-(1-naphthyl)guanidine;
N-(4-chlorobenzoyl)-N'-(4-benzyloxyphenyl)guanidine;
N-(4-chlorobenzoyl)-N'-(4-isopropylphenyl)guanidine;
N-(4-chlorobenzoyl)-N'-(4-tert-butylphenyl)guanidine;
N-(4-chlorobenzoyl)-1-(indolinyl)carboximidamide;
N-(4-chlorobenzoyl)-1-(1,2,3,4-tetrahydroquinolinyl)carboximidamide;
N-(4-chlorobenzoyl)-N'-(2,5-dibromophenyl)guanidine;
N-(3,4-dichlorobenzoyl)-N'-methyl-N'-(3-iodophenyl)guanidine;
N-(3,4-dichlorobenzoyl)-N'-(1-naphthyl)guanidine;
N-(3,4-dichlorobenzoyl)-N'-(4-benzyloxyphenyl)guanidine;
N-(3,4-dichlorobenzoyl)-N'-(4-isopropylphenyl)guanidine;
N-(3,4-dichlorobenzoyl)-N'-(4-tert-butylphenyl)guanidine;
N-(3,4-dichlorobenzoyl)-1-(indolinyl)carboximidamide;
N-3,4-dichlorobenzoyl)-1-(1,2,3,4-tetrahydroquinolinyl)carboximidamide;
N-(3,4-dichlorobenzoyl)-N'-methyl-N'-(4-isopropylphenyl)guanidine;
N-(thiophen-2-carbonyl)-N'-methyl-N'-(3-iodophenyl)guanidine;
N-(thiophen-2-carbonyl)-N'-methyl-N'-(3-methylthiophenyl)guanidine;
N-(thiophen-2-carbonyl)-N'-(1-naphthyl)guanidine;
N-(thiophen-2-carbonyl)-N'-(4-benzyloxyphenyl)guanidine;
N-(thiophen-2-carbonyl)-N'-(4-isopropylphenyl)guanidine;
N-(thiophen-2-carbonyl)-N'-(4-tert-butylphenyl)guanidine;
N-(thiophen-2-carbonyl)-1-(indolinyl)carboximidamide;
N-(thiophen-2-carbonyl)-1-(1,2,3,4-tetrahydroquinolinyl)carboximidamide;
N-(thiophen-2-carbonyl)-N'-methyl-N'-(4-isopropylphenyl)guanidine;
N-(furan-2-carbonyl)-N'-methyl-N'-(3-iodophenyl)guanidine;
N-(furan-2-carbonyl)-N'-methyl-N'-(3-methylthiophenyl)guanidine;
N-(furan-2-carbonyl)-N'-(1-naphthyl)guanidine;
N-(furan-2-carbonyl)-N'-(4-benzyloxyphenyl)guanidine;
N-(furan-2-carbonyl)-N'-(4-isopropylphenyl)guanidine;
N-(furan-2-carbonyl)-N'-(4-tert-butylphenyl)guanidine;
N-(furan-2-carbonyl)-1-(indolinyl)carboximidamide;
N-(furan-2-carbonyl)-1-(1,2,3,4-tetrahydroquinolinyl)carboximidamide;
N-(furan-2-carbonyl)-N'-(4-isopropylphenyl)-N'-methylguanidine;
N-(pyridin-3-carbonyl)-N'-(1-naphthyl)guanidine;
N-(pyridin-3-carbonyl)-N'-(4-benzyloxyphenyl)guanidine;
N-(pyridin-3-carbonyl)-N'-(4-isopropylphenyl)guanidine;
N-(pyridin-3-carbonyl)-N'-(4-tert-butylphenyl)guanidine;
N-(pyridin-3-carbonyl)-1-(indolinyl)carboximidamide;
N-(pyridin-3-carbonyl)-1-(1,2,3,4-tetrahydroquinolinyl)carboximidamide;
N-(4-methoxybenzoyl)-N'-(4-benzyloxyphenyl)guanidine;
N-(4-methoxybenzoyl)-N'-(4-isopropylphenyl)guanidine;
N-(4-methoxybenzoyl)-N'-(4-isopropoxyphenyl)guanidine;
N-(4-methoxybenzoyl)-N'-(3,4,5-trimethoxyphenyl)guanidine;
N-(1-naphthoyl)-N'-(4-benzyloxyphenyl)guanidine;

N-(1-naphthoyl)-N'-(4-isopropylphenyl)guanidine;
N-(1-naphthoyl)-N'-(4-isopropoxyphenyl)guanidine;
N-(3,4,5-trimethoxybenzoyl)-N'-(2-isopropylphenyl)guanidine;
N-(3,4,5-trimethoxybenzoyl)-N'-(4-isopropoxyphenyl)guanidine;
N-(4-butoxybenzoyl)-N'-(2-isopropylphenyl)guanidine;
N-(4-butoxybenzoyl)-N'-(4-isopropoxyphenyl)guanidine;
N-(4-butoxybenzoyl)-N'-(3,4,5-trimethoxyphenyl)guanidine;
N-(4-ethoxybenzoyl)-N'-(2-isopropylphenyl)guanidine;
N-(4-ethoxybenzoyl)-N'-(4-isopropoxyphenyl)guanidine;
N-(4-methylbenzoyl)-N'-(benzyl)guanidine;
N-(4-methylbenzoyl)-N'-(2-phenethyl)guanidine;
N-(4-methylbenzoyl)-N'-(3-dimethylaminopropyl)guanidine;
N-(4-methylbenzoyl)-N'-(4-phenylbutyl)guanidine;
N-(4-methylbenzoyl)-N'-(3-phenylpropyl)guanidine;
N-(4-methylbenzoyl)-N'-(1-naphthylmethyl)guanidine;
N-(4-methylbenzoyl)-N'-(2-(4-chlorophenyl)ethyl)guanidine;
N-(4-methylbenzoyl)-N'-(5-phenylpentyl)guanidine;
N-(4-methylbenzoyl)-N'-(3-phenoxypropyl)guanidine;
N-(3,4-dichlorobenzoyl)-N'-(3-phenylpropyl)guanidine;
N-(4-chlorobenzoyl)-N'-(4-phenylbutyl)guanidine;
N-(4-methoxybenzoyl)-N'-(3-dimethylaminopropyl)guanidine;
N-(4-methoxybenzoyl)-N'-(4-phenylbutyl)guanidine;
N-(4-methoxybenzoyl)-N'-(2-(4-chlorophenylethyl)guanidine;
N-(4-methoxybenzoyl)-N'-(1-naphthylmethyl)guanidine;
N-(4-methoxybenzoyl)-N'-(3,4,5-trimethoxybenzyl)guanidine;
N-(4-ethoxybenzoyl)-N'-(4-phenylbutyl)guanidine;
N-(4-ethoxybenzoyl)-N'-(2-phenethyl)guanidine;
N-(4-ethoxybenzoyl)-N'-(2-(4-chlorophenyl)guanidine;
N-(4-ethoxybenzoyl)-N'-(3-phenylpropyl)guanidine;
N-(4-ethoxybenzoyl)-N'-(1-naphthylmethyl)guanidine;
N-(4-butoxybenzoyl)-N'-(4-phenylbutyl)guanidine;
N-(4-butoxybenzoyl)-N'-(2-phenethyl)guanidine;
N-(4-butoxybenzoyl)-N'-(2-(4-chlorophenyl)ethyl)guanidine;
N-(4-butoxybenzoyl)-N'-(3-phenylpropyl)guanidine;
N-(4-butoxybenzoyl)-N'-(2-(3-indole)ethyl)guanidine;
N-(3,4,5-trimethoxybenzoyl)-N'-(4-phenylbutyl)guanidine;
N-(3,4,5-trimethoxybenzoyl)-N'-(2-(3-indole)ethyl)guanidine;
N-(1-naphthoyl)-N'-(benzyl)guanidine;
N-(1-naphthoyl)-N'-(3-dimethylaminopropyl)guanidine;
N-(1-naphthoyl)-N'-(2-phenylethyl)guanidine;
N-(1-naphthoyl)-N'-(4-phenylbutyl)guanidine;
N-(thiophen-2-carbonyl)-N'-(benzyl)guanidine;
N-(thiophen-2-carbonyl)-N'-(3-dimethylaminopropyl)guanidine;
N-(thiophen-2-carbonyl)-N'-(2-phenylethyl)guanidine;
N-(thiophen-2-carbonyl)-N'-(4-phenylbutyl)guanidine;
N-(4-methylbenzoyl)-N'-(cyclohexyl)-N''-methylguanidine;
N-(4-methylbenzoyl)-N'-(4-phenylbutyl)-N''-methylguanidine;
N-(4-methoxybenzoyl)-N'-(5-phenylpentyl)guanidine;
N-(2-methylbenzoyl)-N'-(4-phenylbutyl)guanidine;
N-(2-methylbenzoyl)-N'-(2-isopropylphenyl)guanidine;
N-(2-methylbenzoyl)-N'-(4-isopropylphenyl)guanidine;
N-(2-methylbenzoyl)-N'-(3-phenylpropyl)guanidine;
N-(4-methoxybenzoyl)-N'-(2-phenoxypropyl)guanidine;
N-(4-butoxybenzoyl)-N'-(5-phenylpentyl)guanidine;
N-(4-methylbenzoyl)-N'-(2-phenoxyethyl)guanidine;
N-(4-methoxybenzoyl)-N'-(2-phenoxyethyl)guanidine;
N-(4-ethoxybenzoyl)-N'-[(2-benzylthio)ethyl]guanidine;
N-(4-ethoxybenzoyl)-N'-(3,4,5-trimethoxyphenyl)guanidine;
or a pharmaceutically acceptable salt of any of said compounds.

* * * * *